(12) United States Patent
Kagumba et al.

(10) Patent No.: US 8,530,044 B2
(45) Date of Patent: Sep. 10, 2013

(54) HYPERBRANCHED OLIGOMERIC PHOSPHONATES AND COMPOSITIONS INCLUDING THE SAME

(75) Inventors: Lawino Kagumba, Cambridge, MA (US); Jan-Pleun Lens, Boston, MA (US); Dieter Freitag, Krefeld (DE)

(73) Assignee: FRX Polymers, Inc., Chelmsford, MA (US)

( * ) Notice: Subject to any disclaimer, the term of this patent is extended or adjusted under 35 U.S.C. 154(b) by 76 days.

(21) Appl. No.: 13/335,146

(22) Filed: Dec. 22, 2011

(65) Prior Publication Data
US 2012/0171460 A1 Jul. 5, 2012

Related U.S. Application Data

(60) Provisional application No. 61/426,341, filed on Dec. 22, 2010.

(51) Int. Cl.
*B32B 3/26* (2006.01)
*B32B 3/06* (2006.01)

(52) U.S. Cl.
USPC ...................................... 428/304.4

(58) Field of Classification Search
USPC .............................. 428/304.4, 461
See application file for complete search history.

(56) References Cited

U.S. PATENT DOCUMENTS

| | | | |
|---|---|---|---|
| 2,716,101 A | 8/1955 | Coover, Jr. et al. |
| 4,039,512 A | 8/1977 | Kim et al. |
| 4,196,119 A | 4/1980 | Evans |
| 4,415,719 A | 11/1983 | Schmidt et al. |
| 4,719,279 A | 1/1988 | Kauth et al. |
| 5,216,113 A | 6/1993 | Schulz-Schlitte et al. |
| 6,861,499 B2 | 3/2005 | Vinciguerra et al. |
| 7,449,526 B2 | 11/2008 | Levchik et al. |
| 7,645,850 B2 | 1/2010 | Freitag |
| 7,816,486 B2 | 10/2010 | Freitag et al. |
| 7,838,604 B2 | 11/2010 | Freitag |
| 2006/0142427 A1 | 6/2006 | Levchik et al. |
| 2009/0032770 A1 | 2/2009 | Freitag et al. |

FOREIGN PATENT DOCUMENTS

JP 2001019746 A 1/2001

OTHER PUBLICATIONS

International Search Report dated Aug. 22, 2012 for PCT/US2011/066881.
International Search Report dated Aug. 27, 2012 for PCT/US2011/066828.

*Primary Examiner* — Terressa Boykin
(74) *Attorney, Agent, or Firm* — Pepper Hamilton LLP

(57) ABSTRACT

Disclosed are oligomeric phosphonates, and in particular, hyperbranched oligophosphonates, that include oligophosphonates, random or block co-oligo(phosphonate ester)s and co-oligo(phosphonate carbonate)s produced using a condensation process terminated with hydroxyl, epoxy, vinyl, vinyl ester, isopropenyl, isocyanate groups, and the like. These materials can be used as a reactive additive to other polymers, oligomers or monomer mixtures to impart flame resistance without diminishing melt processability which is important in the fabrication of polymers for many applications.

37 Claims, No Drawings

HYPERBRANCHED OLIGOMERIC PHOSPHONATES AND COMPOSITIONS INCLUDING THE SAME

CROSS-REFERENCE TO RELATED APPLICATIONS

This application claims priority to U.S. Provisional Application No. 61/426,341, entitled, "Hyperbranched Hydroxy and Epoxy Terminated Oligophosphonates, Co-oligo(Phosphonate Ester)s and Co-oligo(Phosphonate Carbonate)s" filed Dec. 22, 2010, which is incorporated herein by reference in its entirety.

GOVERNMENT INTERESTS

Not Applicable

PARTIES TO A JOINT RESEARCH AGREEMENT

Not Applicable

INCORPORATION BY REFERENCE OF MATERIAL SUBMITTED ON A COMPACT DISC

Not Applicable

BACKGROUND

Not Applicable

SUMMARY OF THE INVENTION

Embodiments of the invention include compositions including hyperbranched oligophosphonates, each hyperbranched oligophosphonate having degree of branching from 0.05 to about 1.0 in which about 40% to about 98% the total of hyperbranched oligophosphonates phosphonates have two or more reactive end-groups. In various embodiments, the reactive end-groups may be hydroxyl end groups, epoxy end groups, carboxylic acid end groups, amine end groups, cyanate end groups, glycidyl end groups, vinyl end groups, vinyl ester end groups, isopropenyl end groups, isocyanate end groups, and combinations thereof, and in particular embodiments, the reactive end groups may be hydroxyl end groups, epoxy end groups, vinyl end groups, vinyl ester end groups, isopropenyl end groups, or isocyanate end groups. In some embodiments, compositions including hyperbranched oligophosphonates may further include linear or lightly branched oligophosphonates.

The hyperbranched oligophosphonates may include oligophosphonates, random co-oligo(phosphonate ester)s, block co-oligo(phosphonate ester)s, random co-oligo(phosphonate carbonate)s, block co-oligo(phosphonate carbonate)s, or combinations thereof in various portions of the hyperbranched oligophosphonate. In some embodiments, the hyperbranched oligophosphonates may have a number averaged molecular weight of from about 500 g/mole to about 5000 g/mole, and in other embodiments, the hyperbranched oligophosphonates may have a number average molecular weight of from about 1500 g/mole to about 3000 g/mole. In certain embodiment, the hyperbranched oligophosphonates or portions thereof may units derived from any bisphenol, and in some embodiments, such unite may be derived from bisphenol A. and in other embodiments, the hyperbranched oligophosphonates or portions thereof may from about 2 to about 20 units derived from a branching agent. In some embodiments, the hyperbranched oligophosphonates or portions thereof may include units of Formula I:

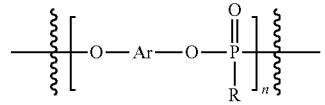

in which Ar is an aromatic group and —O—Ar—O— is derived from resorcinol, hydroquinone, or bisphenol, R is a $C_{1-20}$ alkyl, $C_{2-20}$ alkene, $C_{2-20}$ alkyne, $C_{5-20}$ cycloalkyl, or $C_{6-20}$ aryl, and n is an integer from 1 to about 10. In particular embodiments, —O—Ar—O— may be derived from bisphenol A, bisphenol F, and 4,4'-biphenol, phenolphthalein, 4,4'-thiodiphenol, 4,4'-sulfonyldiphenol, 3,3,5-trimethylcyclohexyldiphenol, or combinations thereof.

In certain embodiments, the hyperbranched oligophosphonates or portions thereof may include a structure of Formula VII:

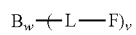

in which B is the hyperbranched oligophosphonate, w is the number of branches, v is an integer that is not zero, L is a linking group comprising an aryl group, heteroaryl group, or a covalent bond, and F is a reactive group. In some embodiment, w may be an integer from 2 to about 10, and v may be an interger of from 1 to about 5. In other embodiments, each F may, independently, be hydroxyl, carboxylic acid, amine, cyanate, isocyanate, epoxy, glycidyl ether, vinyl, vinyl ester, isopropenyl, and the like and combinations thereof. In some embodiments, B may be of a structure of Formula IX or Formula X:

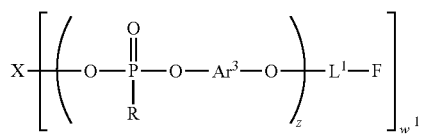

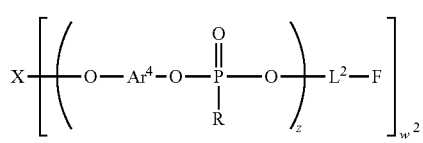

in which each $Ar^3$ and $Ar^4$ is independently an aromatic group and —O—Ar—O— is derived from a dihydroxy compound having one or more aryl rings, each R is, independently, a $C_{1-20}$ alkyl, $C_{2-20}$ alkene, $C_{2-20}$ alkyne, $C_{5-20}$ cycloalkyl, or $C_{6-20}$ aryl, each $L^2$ and $L^2$ is, independently, a covalent bond or single aryl groups, biaryl groups, triaryl groups, tetraaryl groups, each F is, independently, a reactive group, each X is, independently, a unit derived from a branching agent, each z is an integer from 1 to about 10, and each $w^1$ and $w^2$ is, independently, an integer from 1 to 5. In some embodiments, each —O—Ar—O—, including —O—$Ar^3$—O— and —O—$Ar^4$—O—, can be derived from resorcinol, hydroquinone, bisphenol A, bisphenol F, and 4,4'-biphenol, phenolphthalein, 4,4'-thiodiphenol, 4,4'-sulfonyldiphenol, 3,3,5- trimethylcyclohexyldiphenol, or combinations thereof. In other embodiments, R may be a methyl, and in still other embodiments, X may be derived from a triaryl phosphate ester such as, for example, a compound of Formula VIII:

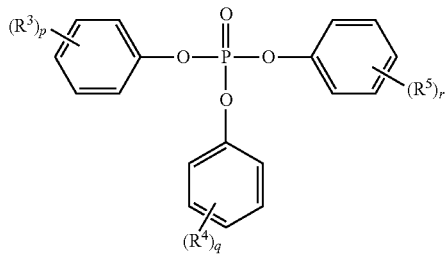

VIII in which each $R^3$, $R^4$, and $R^5$ is, independently, hydrogen, $C_1$-$C_4$ alkyl and each of p, q, and r is, independently, an integer of from 1 to 5. In certain embodiments, X may be derived from triphenyl phosphate. In further embodiments, two or more X can be linked by a moiety of Formula XI, Formula XII, or Formula XIII or combinations thereof:

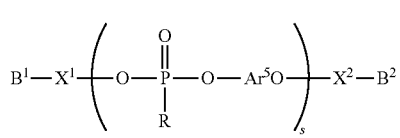

XI

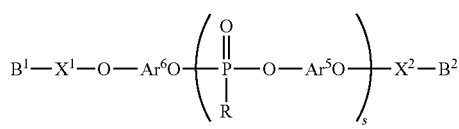

XII

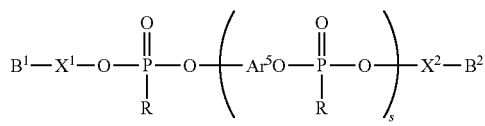

XIII in which each $B^1$ and $B^2$ is, independently, a hyperbranched oligophosphonate of Formula XI or Formula X, each $Ar^5$ and $Ar^6$ is, independently, an aromatic group and —O—Ar—O—, including —O—$Ar^5$—O— and —O—$Ar^6$—O—, is derived from a dihydroxy compound having one or more aryl rings, each R is, independently, a $C_{1-20}$ alkyl, $C_{2-20}$ alkene, $C_{2-20}$ alkyne, $C_{5-20}$ cycloalkyl, or $C_{6-20}$ aryl, each $X^1$ and $X^2$ is, independently, a unit derived from a branching agent and each s is, independently, an integer of from 1 to about 10.

Other embodiments are directed to methods for preparing a hyperbranched oligophosphonate including combining a phosphonate monomer, a branching agent, and co-monomer to create a monomer mixture, the monomer mixture comprising a molar excess of the co-monomer and from about 0.5 mole % to about 10 mole % or greater of the total monomer mixture of the branching agent, heating the monomer mixture, adding a polymerization catalyst to the monomer mixture to create a reaction mixture, and maintaining a polymerization temperature. In some embodiments, the phosphonate monomer may be a monomer of Formula XIV:

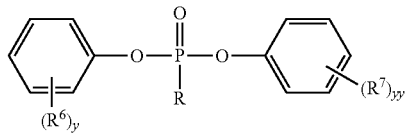

XIV in which each $R^6$ and each $R^7$ are, independently, hydrogen or $C_1$-$C_4$ alkyl, y and yy are, independently, integers of 1 to 5, and R is $C_1$-$C_4$ alkyl or a $C_5$-$C_{10}$ aryl. In certain exemplary embodiments, the phosphonate monomer can be diphenyl methylphosphonic acid, methyldiphenoxyphosphine oxide, or combinations thereof. In some embodiments, the co-monomer may be resorcinol, hydroquinone, bisphenol A, bisphenol F, and 4,4'-biphenol, phenolphthalein, 4,4'-thiodiphenol, 4,4'-sulfonyldiphenol, 3,3,5-trimethylcyclohexyldiphenol, or combinations thereof. In various embodiments, the polymerization catalyst may be tetraphenylphosphonium or a derivative thereof including an anion associated with the tetraphenylphosphonium that can be, for example, tetraaryl borohydride, halide, or a substituted or unsubstituted phenolate group, and in some embodiments, the polymerization may be tetraphenylphosphonium phenolate. In particular embodiments, heating the monomer mixture and polymerization catalyst may be carried out at a reduced pressure, and in some embodiments, heating the reaction mixture may be carried out to a temperature of from about 100° C. to about 350° C., and a temperature within this range may be maintained throughout the method. Certain embodiments include stopping heating when the evolution of phenol has stopped. In various embodiments, the at least one branching agent may be, for example, trimesic acid, pyromellitic acid, trimellitic anhydride, pyromellitic anhydride, trimethylolpropane, dimethyl hydroxyl terephthalate, pentaerythritol, phloroglucinol, 4,6-dimethyl-2,4,6-tri-(4-hydroxy phenyl)-2-heptene, 4,6-dimethyl-2,4,6-tri-(4-hydroxy phenyl)-heptane, 1,3,5-tri-(4-hydroxy phenyl)-benzene, 1,1,1-tri-(4-hydroxy phenyl)-ethane, tri-(4-hydroxy phenyl)-phenyl methane, 2,2-bis-[4,4-bis-(4-hydroxy phenyl)-cyclohexyl]-propane, 2,4-bis-(4-hydroxy phenyl)isopropyl phenol, 2,6-bis-(2'-hydroxy-5'-methyl benzyl)-4-methyl phenol 2-(4-hydroxy phenyl)-2-(2,4-dihydroxy phenol)-propane, tetra-(4-hydroxy phenyl) methane, tetra-[4-(4-hydroxy phenyl isopropyl)phenoxy]-methane, 1,4-bis-(4,4"-dihydroxy triphenyl methyl)-benzene, or combinations thereof. In some embodiments, the monomer mixture may further include oligocarbonates, carbonate monomers, oligoesters, ester monomers, or combinations thereof, and in such embodiments, the carbonate monomer may be, for example, diphenyl carbonate, 4-tert-butylphenyl-phenyl carbonate, di-(4-tert-butylphenyl) carbonate, biphenyl-4-yl-phenyl carbonate, di-(biphenyl-4-yl)carbonate, 4-(1-methyl-1-phenylethyl)-phenyl-phenyl carbonate, di-[4-(1-methyl-1-phenylethyl)-phenyl]carbonate, or combinations thereof.

Other embodiments include methods for preparing hyperbranched oligophosphonates including providing a predominately hydroxyl terminated hyperbranched oligophosphonate, combining the predominately hydroxyl terminated hyperbranched oligophosphonate with an effective amount of epichlorohydrin, and maintaining reaction conditions to create a predominately epoxy terminated oligophosphonate. The effective amount of epichlorohydrin may vary among embodiments and may be from at a ratio of about 1:2 to about 1:10 hyperbranched oligophosphonates to epichlorohydrin. In some embodiments, the predominately hydroxyl terminated hyperbranched oligophosphonate or portions thereof may include an oligophosphonate, random co-oligo(phosphonate ester), block co-oligo(phosphonate ester), random co-oligo(phosphonate carbonate), or block co-oligo(phosphonate carbonate).

Yet other embodiments are directed to polymer compositions including hyperbranched oligophosphonates, each hyperbranched oligophosphonate having degree of branching from 0.05 to about 1.0 in which about 40% to about 98% the total of hyperbranched oligophosphonates have two or more reactive end-groups, and an engineering polymer. The engineering polymer of various embodiments may include polycarbonates, epoxies, epoxy derived polymers, polyepoxies, benzoxazines, polyacrylates, polyacrylonitriles, polyesters, poly(ethylene terephthalate), poly(trimethylene terephthalate), poly(butylene terephthalate), unsaturated polyesters, polyamides, polystyrenes, high impact strength polystyrene, polyureas, polyurethanes, polyphosphonates, polyphosphates, poly(acrylonitrile butadiene styrene)s, polyimides, polyarylates, poly(arylene ether)s, polyethylenes, polypropylenes, polyphenylene sulfides, poly(vinyl ester)s, polyvinyl chlorides, bismaleimide polymers, polyanhydrides, liquid crystalline polymers, cellulose polymers, or combination thereof. Is some embodiments, the polymer compositions may further include, for example, fillers, chopped or continuous glass fiber, metal fibers, organic fibers, aramid fibers, carbon fibers, carbon nanofibers, or ceramic fibers, surfactants, organic binders, polymeric binders, crosslinking agents, coupling agents, diluents, anti-dripping agents, fluorinated polyolefins, silicones, lubricants, mould release agents, pentaerythritol tetrastearate, nucleating agents, anti-static agents, conductive blacks, carbon nanotubes, organic antistatics, polyalkylene ethers, alkylsulfonates, perfluor sulfonic acid, perfluorbutane sulfinic acid potassium salt, polyamide-containing polymers, catalysts, colorants, inks, dyes, antioxidants, stabilizers, metal phosphinates, melamine cyanurate, melamine derivatives, flame retardants, or combinations thereof.

Further embodiments are directed to articles of manufacture including hyperbranched oligophosphonates, each hyperbranched oligophosphonate having degree of branching from 0.05 to about 1.0 in which about 40% to about 98% the total of hyperbranched oligophosphonates phosphonates have two or more reactive end-groups. The articles of manufacture of various embodiments may be coatings on plastics, coatings on metals, coatings on ceramic, coatings on wood products, free-standing films, fibers, foams, molded articles, fiber reinforced composites, support parts, electrical components, electrical connectors, laminated boards, laminated circuit boards, printed wiring laminated boards, housings, sub-components and components for electrical devices, televisions, computers, laptop computers, printers, cell phones, video games, DVD players, and stereos. In certain embodiments, the articled of manufacture may be a laminate or a fiber reinforced composite used in electrical components, electrical connectors, printed wiring boards, printed circuit boards, televisions, computers, laptop computers, printers, copiers, scanners, cell phones, video games, DVD players, stereos, digital music players, hand held video players, touch screens, and other such electronic devices.

DESCRIPTION OF DRAWINGS

Not Applicable

DETAILED DESCRIPTION

The above summary of the present invention is not intended to describe each illustrated embodiment or every possible implementation of the present invention. The detailed description, which follows, particularly exemplifies these embodiments.

Before the present compositions and methods are described, it is to be understood that they are not limited to the particular compositions, methodologies or protocols described, as these may vary. It is also to be understood that the terminology used in the description is for the purpose of describing the particular versions or embodiments only, and is not intended to limit their scope which will be limited only by the appended claims.

It must also be noted that as used herein and in the appended claims, the singular forms "a", "an", and "the" include plural reference unless the context clearly dictates otherwise. Unless defined otherwise, all technical and scientific terms used herein have the same meanings as commonly understood by one of ordinary skill in the art. Although any methods and materials similar or equivalent to those described herein can be used in the practice or testing of embodiments disclosed, the preferred methods, devices, and materials are now described.

"Optional" or "optionally" means that the subsequently described event or circumstance may or may not occur, and that the description includes instances where the event occurs and instances where it does not.

"Substantially no" means that the subsequently described event may occur at most about less than 10% of the time or the subsequently described component may be at most about less than 10% of the total composition, in some embodiments, and in others, at most about less than 5%, and in still others at most about less than 1%.

The term "carbonate" as used herein is given its customary meaning, e.g., a salt of carbonic acid containing the divalent, negative radical CO or an uncharged ester of this acid. A "diaryl carbonate" is a carbonate with at least two aryl groups associated with the CO radical, the most predominant example of a diaryl carbonate is diphenyl carbonate; however, the definition of diaryl carbonate is not limited to this specific example.

The term "aromatic dihydroxide" is meant to encompass any aromatic compound with at least two associated hydroxyl substitutions. Examples of "aromatic hydroxides" include but are not limited to benzene diols such as hydroquinone and any bisphenol or bisphenol containing compounds.

The term "alkyl" or "alkyl group" refers to a branched or unbranched hydrocarbon or group of 1 to 20 carbon atoms, such as but not limited to methyl, ethyl, n-propyl, isopropyl, n-butyl, isobutyl, t-butyl, octyl, decyl, tetradecyl, hexadecyl, eicosyl, tetracosyl and the like. "Cycloalkyl" or "cycloalkyl groups" are branched or unbranched hydrocarbons in which all or some of the carbons are arranged in a ring such as but not limited to cyclopentyl, cyclohexyl, methylcyclohexyl and the like. The term "lower alkyl" includes an alkyl group of 1 to 10 carbon atoms.

The term "aryl" or "aryl group" refers to monovalent aromatic hydrocarbon radicals or groups consisting of one or more fused rings in which at least one ring is aromatic in nature. Aryls may include but are not limited to phenyl, napthyl, biphenyl ring systems and the like. The aryl group may be unsubstituted or substituted with a variety of substituents including but not limited to alkyl, alkenyl, halide, benzylic, alkyl or aromatic ether, nitro, cyano and the like and combinations thereof.

"Substituent" refers to a molecular group that replaces a hydrogen in a compound and may include but are not limited to trifluoromethyl, nitro, cyano, $C_1$-$C_{20}$ alkyl, aromatic or aryl, halide (F, Cl, Br, I), $C_1$-$C_{20}$ alkyl ether, $C_1$-$C_{20}$ alkyl ester, benzyl halide, benzyl ether, aromatic or aryl ether, hydroxy, alkoxy, amino, alkylamino (—NHR'), dialkylamino (—NR'R") or other groups which do not interfere with the formation of the diaryl alkylphosphonate.

As defined herein, an "arylol" or an "arylol group" is an aryl group with a hydroxyl, OH, group substituent on the aryl ring. Non-limiting examples of an arylol are phenol, naphthol, and the like. A wide variety of arlyols may be used in the embodiments of the invention and are commercially available.

The term "alkanol" or "alkanol group" refers to a compound including an alkyl of 1 to 20 carbon atoms or more having at least one hydroxyl group substituent. Examples of alkanols include but are not limited to methanol, ethanol, 1- and 2-propanol, 1,1-dimethylethanol, hexanol, octanol and the like. Alkanol groups may be optionally substituted with substituents as described above.

The term "alkenol" or "alkenol group" refers to a compound including an alkene 2 to 20 carbon atoms or more having at least one hydroxyl group substituent. The hydroxyl may be arranged in either isomeric configuration (cis or trans). Alkenols may be further substituted with one or more substituents as described above and may be used in place of alkanols in some embodiments of the invention. Alkenols are known to those skilled in the art and many are readily available commercially.

The terms "flame retardant," "flame resistant," "fire resistant," or "fire resistance," as used herein, means that the composition exhibits a limiting oxygen index (LOI) of at least 27. "Flame retardant," "flame resistant," "fire resistant," or "fire resistance," may also be tested by measuring the afterburning time in accordance with the UL test (Subject 94). In this test, the tested materials are given classifications of UL-94 V-0, UL-94 V-1 and UL-94 V-2 on the basis of the results obtained with the ten test specimens. Briefly, the criteria for each of these UL-94-V-classifications are as follows:

UL-94 V-0: the total flaming combustion for each specimen after removal of the ignition flame should not exceed 10 seconds and the total flaming combustion for 5 specimens should not exceed 50 seconds. None of the test specimens should release and drips which ignite absorbent cotton wool.

UL-94 V-1: the total flaming combustion for each specimen after removal of the ignition flame should not exceed 30 seconds and the total flaming combustion for 5 specimens should not exceed 250 seconds. None of the test specimens should release any drips which ignite absorbent cotton wool.

UL-94 V-2: the total flaming combustion for each specimen after removal of the ignition flame should not exceed 30 seconds and the total flaming combustion for 5 specimens should not exceed 250 seconds. Test specimens may release flaming particles, which ignite absorbent cotton wool.

Fire resistance may also be tested by measuring afterburning time. These test methods provide a laboratory test procedure for measuring and comparing the surface flammability of materials when exposed to a prescribed level of radiant heat energy to measure the surface flammability of materials when exposed to fire. The test is conducted using small specimens that are representative, to the extent possible, of the material or assembly being evaluated. The rate at which flames travel along surfaces depends upon the physical and thermal properties of the material, product or assembly under test, the specimen mounting method and orientation, the type and level of fire or heat exposure, the availability of air, and properties of the surrounding enclosure. If different test conditions are substituted or the end-use conditions are changed, it may not always be possible by or from this test to predict changes in the fire-test-response characteristics measured. Therefore, the results are valid only for the fire test exposure conditions described in this procedure.

The state-of-the-art approach to rendering polymers flame retardant is to use additives such as brominated compounds or compounds containing aluminum and/or phosphorus. Use of the additives with polymer can have a deleterious effect on the processing characteristics and/or the mechanical performance of articles produced from them. In addition, some of these compounds are toxic, and can leach into the environment over time making their use less desirable. In some countries, certain brominated additives are being phased-out of use because of environmental concerns.

"Molecular weight," as used herein, can be determined by relative viscosity ($\eta_{rel}$) and/or gel permeation chromatography (GPC). "Relative viscosity" of a polymer is measured by dissolving a known quantity of polymer in a solvent and comparing the time it takes for this solution and the neat solvent to travel through a specially designed capillary (viscometer) at a constant temperature. Relative viscosity is a measurement that is indicative of the molecular weight of a polymer. It is also well known that a reduction in relative viscosity is indicative of a reduction in molecular weight, and reduction in molecular weight causes loss of mechanical properties such as strength and toughness. GPC provides information about the molecular weight and molecular weight distribution of a polymer. It is known that the molecular weight distribution of a polymer is important to properties such as thermo-oxidative stability (due to different amount of end groups), toughness, melt flow, and fire resistance, for example, low molecular weight polymers drip more when burned.

The term "toughness," as used herein, is meant to imply that the material is resistant to breaking or fracturing when stressed or impacted. There are a variety of standardized tests available to determine the toughness of a material. Generally, toughness is determined qualitatively using a film or a molded specimen.

The phrase "low viscosity when sheared," "shear thinning," or similar phrases, as used herein, is meant to imply that when the material is melted and subjected to a shearing force, such as that encountered with certain types of mixers or when the melt is forced with pressure through a die or body having similar orifice, the viscosity is reduced. Shear thinning behavior may be transferred to blends of materials. Thus, the blend of, for example, the hyperbranched oligophosphonates or co-oligo(phosphonate carbonate)s and a thermoplastic, may exhibit shear thinning, while the thermoplastic alone or a blend of a thermoplastic and a linear or lightly branched oligophosphonate or co-oligo(phosphonate carbonate) do not. Shear thinning can be measured using standardized methods such as the Shear Thinning Index (STI). STI represents the ratio of the viscosity at a low rpm shear to the viscosity at a high rpm, generally, about ten times the low rotational speed. For example, low shear may be 1 rpm and high shear can be 10 rpm. The higher the STI value, the more shear thinning the material exhibits.

Embodiments of the invention are directed to reactive oligophosphonates, random or block co-oligo(phosphonate ester)s, and random or block co-oligo(phosphonate carbonate)s, methods for making these oligomeric phosphonates, polymer compositions including such oligomeric phosphonates and another monomer, oligomer, or polymer, methods for preparing such compositions, articles of manufacture including oligomeric phosphonates, and articles of manufacture including polymer compositions. In various embodiments, the reactive oligophosphonates, random or block co-oligo(phosphonate ester)s and co-oligo(phosphonate carbonate)s may include reactive end groups such as, for example, hydroxyl end groups, epoxy end groups, isocyanate end groups, vinyl end groups, vinyl ester end groups, isopropenyl end groups, and the like and combinations thereof. In some embodiments, the reactive end groups may allow the oligomeric phosphonates to react chemically with other monomers, oligomers, or polymers in polymer compositions leading to crosslinking or chain extension or a combination thereof. For example, reactive end groups such as hydroxyl end groups, epoxy end groups, vinyl end groups, vinyl ester end groups, isopropenyl end groups, or isocyanate end groups are capable of reacting with functional groups such as, but not limited to, alcohols, carboxylic acids and salts thereof, anhydrides, acyl chlorides, epoxides, aldehydes, ketones, amines, thiols, Grignard reagents, vinyl groups, acetylene groups and sodium hydroxide acids and salts thereof. When monomers, oligomers, or polymers including these functional groups are combined with oligomeric phosphonates having hydroxyl end groups, epoxy end groups, vinyl end groups, vinyl ester end groups, isopropenyl end groups, or isocyanate end groups crosslinking or chain extension or a combination of both may occur. The reactive oligophosphonates, random or block co-oligo(phosphonate ester)s, and random or block co-oligo(phosphonate carbonate)s may thereby impart flame resistance while not detracting from the mechanical properties of the base polymer of the polymer composition.

The oligomeric phosphonates of such embodiments may be linear or branched, and in certain embodiments, the oligomeric phosphonates may be hyperbranched. In general, the concentration of reactive end groups based on the total number of termini for the oligomeric phosphonates may be high. For example, oligomeric phosphonates may have a percentage of the total number of termini having reactive end groups of from about 80% to 100%, about 85% to about 99%, or about 90% to about 98%. In other embodiments, greater than 90% of the total termini of the oligomeric phosphonate may have a reactive end group. For branched or hyperbranched oligomeric phosphonates of other embodiments, the percentage of the total number of termini having reactive end groups may be from about 50% to 100%, about 75% to about 95%, or about 80% to about 90%, and in certain embodiments, greater than 80% of the total termini for a branched or hyperbranched oligomeric phosphonate may have a reactive end group.

For simplicity, throughout this disclosure, the terms, "oligomeric phosphonates," "phosphonate oligomers," and the like are to be construed as referring to any type of oligomer described herein including oligophosphonates, random or block co-oligo(phosphonate ester)s, and random or block co-oligo(phosphonate carbonate)s. Such oligomers encompassed by these terms can be linear, lightly branched, indicating a relatively small number of branches, for example, 1 to about 5 branches per oligomer, or hyperbranched, indicating a relatively high number of branches, for example, greater than 5. While individual types of oligomers may be called out in specific exemplary embodiments, any oligomeric phosphonate described herein can be used in such exemplary embodiments. For example, an exemplary stating that an oligomeric phosphonate is used can be carried out with a linear, lightly branched, or hyperbranched oligomeric phosphonate that can be an oligophosphonate, random or block co-oligo(phosphonate ester), and random or block co-oligo(phosphonate carbonate) type oligomeric phosphonate.

Embodiments of the invention are not limited by the type of oligophosphonate, co-oligo(phosphonate ester), or co-oligo(phosphonate carbonate), and in certain embodiments, the oligophosphonate, co-oligo(phosphonate ester), or co-oligo(phosphonate carbonate) may have the structures described and claimed in U.S. Pat. Nos. 6,861,499, 7,816,486, 7,645,850, and 7,838,604 and U.S. Publication No. 2009/0032770, each of which are hereby incorporated by reference in their entireties. Briefly, such oligomers may include repeating units derived from diaryl alkylphosphonates or diaryl arylphosphonates. For example, in some embodiments, such phosphonate oligomers include structural units illustrated by Formula I:

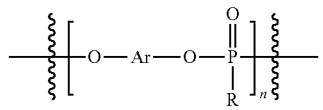

where Ar is an aromatic group and —O—Ar—O— may be derived from a dihydroxy compound having one or more, optionally substituted, aryl rings such as, but not limited to, resorcinols, hydroquinones, and bisphenols, such as bisphenol A, bisphenol F, and 4,4'-biphenol, phenolphthalein, 4,4'-thiodiphenol, 4,4'-sulfonyldiphenol, 3,3,5-trimethylcyclohexyldiphenol, or combinations of these, R is a $C_{1-20}$ alkyl, $C_{2-20}$ alkene, $C_{2-20}$ alkyne, $C_{5-20}$ cycloalkyl, or $C_{6-20}$ aryl, and n is an integer from 1 to about 20, 1 to about 10, or 2 to about 5, or any integer between these ranges.

In other embodiments, the co-oligo(phosphonate carbonate), or co-oligo(phosphonate ester), may have structures such as, but not limited to, those structures of Formulae II and III, respectively:

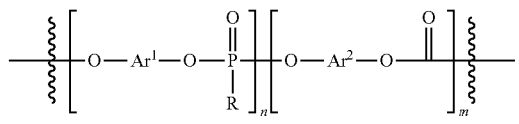

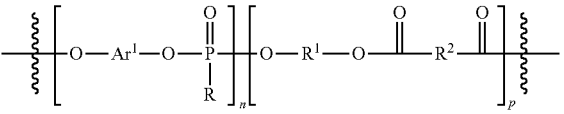

and combinations thereof, where Ar, $Ar^1$, and $Ar^2$ are each, independently, an aromatic group and —O—Ar—O— may be derived from a dihydroxy compound having one or more, optionally substituted, aryl rings such as, but not limited to, resorcinols, hydroquinones, and bisphenols, such as bisphenol A, bisphenol F, and 4,4'-biphenol, phenolphthalein, 4,4'-thiodiphenol, 4,4'-sulfonyldiphenol, 3,3,5-trimethylcyclohexyldiphenol, or combinations of these, R is a $C_{1-20}$ alkyl, $C_{2-20}$ alkene, $C_{2-20}$ alkyne, $C_{5-20}$ cycloalkyl, or $C_{6-20}$ aryl, $R^1$ and $R^2$ are aliphatic or aromatic hydrocarbons, and each m, n, and p can be the same or different and can, independently, be an integer from 1 to about 20, 1 to about 10, or 2 to about 5, or any integer between these ranges. In certain embodiments, each m, n and p are about equal and generally greater than 5 or less than 15.

As indicated by the term "random" the monomers of the "random co-oligo(phosphonate carbonate)s" or "random co-oligo(phosphonate ester)s of various embodiments are incorporated into polymer chain randomly, such that the oligomeric phosphonate chain can include alternating phosphonate and carbonate or ester monomers or short segments in which several phosphonate or carbonate or ester monomers are linked by an aromatic dihydroxide. The length of such segments may vary within individual random co-oligo(phosphonate carbonate)s or co-oligo(phosphonate ester).

In particular embodiments, the Ar, $Ar^1$, and $Ar^2$ may be bisphenol A and R may be a methyl group providing oligomeric phosphonates having reactive end-groups including random and block co-oligo(phosphonate carbonate)s and co-oligo(phosphonate ester)s. Such compounds may have structures such as, but not limited to, structures of Formulae IV, V, and IV:

and one or more aromatic dihydroxide, wherein the mole percent of the high purity diaryl alkylphosphonate is based on the total amount of transesterification components.

The phosphonate and carbonate content of the oligomeric phosphonates, random or block co-oligo(phosphonate carbonate)s and co-oligo(phosphonate ester)s may vary among embodiments, and embodiments are not limited by the phosphonate and/or carbonate content or range of phosphonate and/or carbonate content. For example, in some embodiments, the co-oligo(phosphonate carbonate)s or co-oligo (phosphonate ester)s may have a phosphorus content, of from about 1% to about 12% by weight of the total oligomer, and in

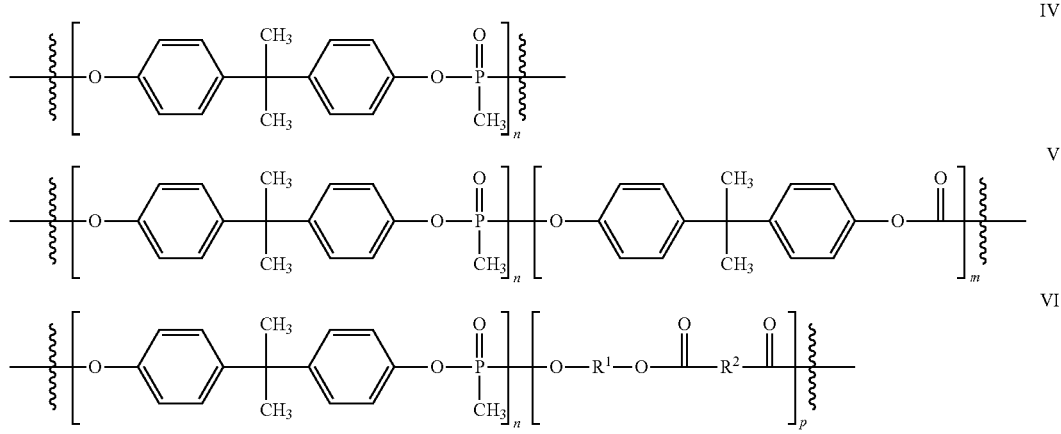

and combinations thereof, where each of m, n, p, and $R^1$ and $R^2$ are defined as described above. Such co-oligo(phosphonate ester), or co-oligo(phosphonate carbonate) may be block co-oligo(phosphonate ester), block co-oligo(phosphonate carbonate) in which each m, n, and p is greater than about 1, and the copolymers contain distinct repeating phosphonate and carbonate blocks or phosphonate and ester blocks. In other embodiments, the oligomeric co-oligo(phosphonate ester) or co-oligo(phosphonate carbonate) can be random copolymers in which each m, n, and p can vary and may be from n is an integer from 1 to about 20, 1 to about 10, or 2 to about 5, where the total of m, n, and p is an integer from 1 to about 20, 1 to about 10, or 2 to about 5 or any integer between these ranges.

With particular regard to co-oligo(phosphonate ester)s, co-oligo(phosphonate carbonate)s, block co-oligo(phosphonate ester)s, and block co-oligo(phosphonate carbonate)s, without wishing to be bound by theory, oligomers containing carbonate components, whether as carbonate blocks or randomly arranged carbonate monomers, may provide improved toughness over oligomers derived solely from phosphonates. Such co-oligomers may also provide higher glass transition temperature, $T_g$, and better heat stability over phosphonate oligomers.

The co-oligo(phosphonate carbonate)s of certain embodiments may be synthesized from at least 20 mole % diaryl alkylphosphonate or optionally substituted diaryl alkylphosphonate, one or more diaryl carbonate, and one or more aromatic dihydroxide, wherein the mole percent of the high purity diaryl alkylphosphonate is based on the total amount of transesterification components, i.e., total diaryl alkylphosphonate and total diaryl carbonate. Likewise, co-oligo(phosphonate ester)s of certain embodiments may be synthesized from at least 20 mole % diaryl alkylphosphonate or optionally substituted diaryl alkylphosphonate, one or more diaryl ester, other embodiments, the phosphorous content may be from about 2% to about 10% by weight of the total oligomer.

In some embodiments, the molecular weight (weight average molecular weight as determined by gel permeation chromatography based on polystyrene calibration) range of the oligophosphonates, random or block co-oligo(phosphonate ester)s and co-oligo(phosphonate carbonate)s may be from about 500 g/mole to about 18,000 g/mole or any value within this range. In other embodiments, the molecular weight range may be from about 1500 g/mole to about 15,000 g/mole, about 3000 g/mole to about 10,000 g/mole, or any value within these ranges. In still other embodiments, the molecular weight range may be from about 700 g/mole to about 9000 g/mole, about 1000 g/mole to about 8000 g/mole, about 3000 g/mole to about 4000 g/mole, or any value within these ranges.

Hyperbranched oligomers of various embodiments have a highly branched structure and a high degree of functionality (i.e., chemical reactivity). The branched structure of such hyperbranched oligomers creates a high concentration of terminal groups, one at the end of nearly every branch that can include a reactive functional group such as hydroxyl end groups, epoxy end groups, vinyl end groups, vinyl ester end groups, isopropenyl end groups, isocyanate end groups, and the like. In some embodiments, the hyperbranched oligomers may have a unique combination of chemical and physical properties when compared to linear oligomeric phosphonates. For example, the high degree of branching can prevent crystallization and can render chain entanglement unlikely, so the hyperbranched oligomers can exhibit solubility in organic solvents and low solution viscosity and melt viscosity especially when sheared.

In some embodiments, the hyperbranched oligomers can contain branches that are not perfectly (i.e., absolutely regular) arranged. For example, various branches on a single hyperbranched oligomer may have different lengths, functional group composition, and the like and combinations thereof. Consequently, in some embodiments, the hyperbranched oligomers of the invention can have a broad molecular weight distribution. In other embodiments, the hyperbranched oligomers of the invention may be perfectly branched, including branches that are nearly identical, and have a monodisperse molecular weight distribution.

The degree of branching for the hyperbranched oligomers of the invention can be defined as the number average fraction of branching groups per molecule, i.e., the ratio of terminal groups plus branch monomer units to the total number of terminal groups, branch monomer units, and linear monomer units. For linear oligomers, the degree of branching as defined by the number average fraction of branching groups per molecule is zero, and for ideal dendrimers, the degree of branching is one. Hyperbranched oligomers can have a degree of branching which is intermediate between that of linear oligomers and ideal dendrimers. For example, a degree of branching for hyperbranched oligomers may be from about 0.05 to about 1, about 0.25 to about 0.75, or about 0.3 to about 0.6, and in certain embodiments, the hyperbranched oligomers may have a number average fraction of branching groups about 0.5.

The hyperbranched oligomers of the invention may be generically represented by the following structure Formula VII:

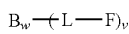

VII where B is the hyperbranched oligomer and w is the number of branches, v is an integer that is not zero, L is a linking group, and F is a reactive group.

The linking group (L) can be any moiety compatible with the chemistry of the monomers for the oligophosphonate, co-oligo(phosphonate ester), or co-oligo(phosphonate carbonate) described above. For example, in some embodiments, L can be any unit derived from an aryl or heteroaryl group including single aryl groups, biaryl groups, triaryl groups, tetraaryl groups, and so on. In other embodiments, L can be a covalent bond linking a functional group (F) directly to the hyperbranched oligomer, and in still other embodiments, L can be a $C_1$-$C_{10}$ alkyl, $C_2$-$C_{10}$ alkene, or $C_2$-$C_{10}$ alkyne that may or may not be branched.

The linking group (L) allows for attachment of one or more functional groups (F) to each branch termination of the hyperbranched oligomer. In some embodiments, each branch termination may have an attached linking group, and in other embodiments, one or more branch terminations of the hyperbranched oligomer (B) may not have an attached linking group. Such branch terminations without an attached linking group may terminate in a hydroxyl group or phenol group associated with the monomeric units of the hyperbranched oligomer. For branch terminations that include a linking group (L), each linking group may have from 0 to 5 or more associated functional groups. Thus, in some embodiments, one or more linking group of the reactive hyperbranched oligomer may have no attached functional groups, such that the branch termination associated with this linking group is substantially unreactive. In other embodiments, one or more linking group of the reactive hyperbranched oligomer may have one or more attached functional groups providing a branch termination that is potentially reactive with other monomers, oligomers, or polymers, and in still other embodiments, one or more linking groups of the reactive hyperbranched oligomer can have multiple attached functional groups. For example, two of the aryl groups associated with a triaryl group may include a functional group (F) with the third aryl group attaching the linking group to the hyperbranched polymer or oligomer. The functional group (F) may vary among embodiments and can be any chemical moiety capable of reacting with another chemical moiety. Non-limiting examples of functional groups (F) include hydroxyl, carboxylic acid, amine, cyanate, isocyanate, epoxy, glycidyl ether, vinyl, and the like and combinations thereof. The reactive hyperbranched oligomers of the present invention are reactive with a variety of functional groups such as epoxies, anhydrides, activated halides, carboxylic acids, carboxylic esters, isocyanates, aldehydes, vinyls, acetylenes, and silanes. These groups may be present on another monomer, oligomer, or polymer used in the preparation of a polymer composition.

The hyberbranched oligomer portion (B) of the general structure presented above may be any phosphonate containing hyperbranched oligomer. For example, in some embodiments, such hyperbranched oligomers may include repeating units derived from diaryl alkyl- or diaryl arylphosphonates, and certain embodiments, such hyperbranched oligomers may have a structure including units of Formula I:

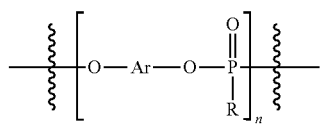

I where Ar is an aromatic group and —O—Ar—O— may be derived from a compound having one or more, optionally substituted, aryl rings such as, but not limited to, resorcinols, hydroquinones, and bisphenols, such as bisphenol A, bisphenol F, and 4,4'-biphenyl, phenolphthalein, 4,4'-thiodiphenol, 4,4'-sulfonyldiphenol, 3,3,5-trimethylcyclohexyldiphenol, or combinations of these, R is a $C_{1-20}$ alkyl, $C_{2-20}$ alkene, $C_{2-20}$ alkyne, $C_{5-20}$ cycloalkyl, or $C_{6-20}$ aryl, and n is an integer from 1 to about 20, 1 to about 10, or 2 to about 5, or any integer between these ranges.

The hyperbranched oligomers (B) of such embodiments may further include units derived from branching agents or multifunctional aryl multifunctional biaryl groups, multifunctional triaryl groups, multifunctional tetra aryl, and so on. In some embodiments, the units derived from branching agents may be derived from, for example, polyfunctional acids, polyfunctional glycols, or acid/glycol hybrids. In other embodiments, the hyperbranched oligomeric phosphonates may have units derived from tri or tetrahydroxy aromatic compounds or triaryl or tetraaryl phosphoric acid esters, triaryl or tetraaryl carbonate or triaryl or tetraaryl esters or combinations thereof such as, but not limited to, trimesic acid, pyromellitic acid, trimellitic anhydride, pyromellitic anhydride, trimethylolpropane, dimethyl hydroxyl terephthalate, pentaerythritol, and the like and combinations thereof. Such branching agents provide branch points within the hyperbranched oligomeric phosphonate. In particular embodiments, the branching agent may be a triaryl phosphate such as, for example, those of Formula VIII:

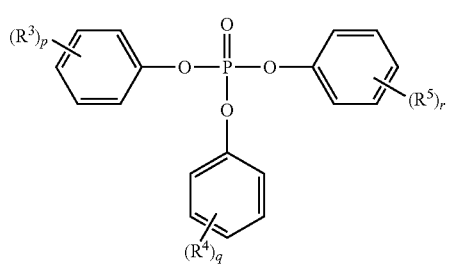

VIII where each $R^3$, $R^4$, and $R^5$ can, independently, be a hydrogen, $C_1$-$C_4$ alkyl of, and each of p, q, and r are independently integers of from 1 to 5.

The number of branches (w) may be directly proportional to the number of units derived from a branching agent and may be any integer from about 2 to about 20. In some embodiments, n may be an integer greater than 3, greater than 5, or greater than 10 or any value within these ranges, and in other embodiments, n may be from about 5 to about 20, about 5 to about 15, about 5 to about 10, or any value between these ranges.

The reactive hyperbranched phosphonates of certain embodiments may have a structure in which B is of Formula IX or Formula X:

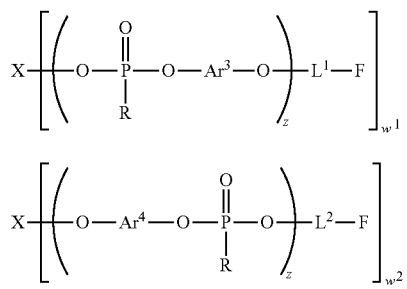

where each $Ar^3$ and $Ar^4$ are, independently, an aromatic group and —O—$Ar^3$—O— and —O—$Ar^4$—O— can be derived from a dihydroxy compound having one or more, optionally substituted, aryl rings such as, but not limited to, resorcinols, hydroquinones, and bisphenols, such as bisphenol A, bisphenol F, and 4,4'-biphenol, phenolphthalein, 4,4'-thiodiphenol, 4,4'-sulfonyldiphenol, 3,3,5-trimethylcyclohexyldiphenol, or combinations of these, each $L^1$ and $L^2$ are, independently, a covalent bond or an aryl or heteroaryl group including single aryl groups, biaryl groups, triaryl groups, tetraaryl groups, and so on, R can be a $C_{1-20}$ alkyl, $C_{2-20}$ alkene, $C_{2-20}$ alkyne, $C_{5-20}$ cycloalkyl, or $C_{6-20}$ aryl, z is an integer from 1 to about 20, 1 to about 10, or 2 to about 5, or any integer between these ranges, and each $w^1$ and $w^2$ are, independently, 1 to 5. X may be derived from any branching agent described above. In some embodiments, X in an individual B may be the same molecule, such that branches having a structure of Formula VII and Formula VII may extend from the same branching agent (X) molecule. In particular embodiments, X may be an triarylphosphate of Formula VIII as described above. In other embodiments, two or more X may be linked as illustrated in Formula XI, Formula XII, or Formula XIII:

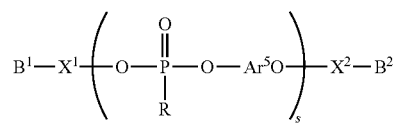

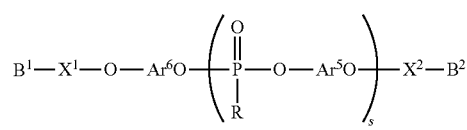

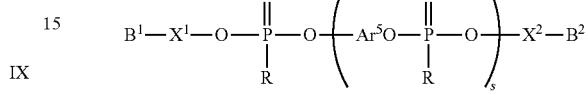

where each $B^1$ and $B^2$ are, independently, hyperbranched polymers as described above, each $X^1$ and $X^2$ are, independently, branching agents as described above, each $Ar^5$ and $Ar^6$ are, independently, an aromatic group and —O—$Ar^5$—O— and —O—$Ar^6$—O— can be derived from a dihydroxy compound having one or more, optionally substituted, aryl rings such as, but not limited to, resorcinols, hydroquinones, and bisphenols, such as bisphenol A, bisphenol F, and 4,4'-biphenol, phenolphthalein, 4,4'-thiodiphenol, 4,4'-sulfonyldiphenol, 3,3,5-trimethylcyclohexyldiphenol or combinations of these, each R is as defined as above, and s is an integer of from 1 to about 20, 1 to about 10, or 2 to about 5, or any integer therebetween. In various embodiments, an individual reactive hyperbranched oligomer may have a structure in which portions of the oligomer can be any of Formula I, and VIII to XIII. Thus, embodiments encompass reactive hyperbranched oligomers in having any combination of the Formulae provided above. In other embodiments, a reactive hyperbranched oligomer may be composed of substantially one or two structures of the Formulae presented above. For example, a hyperbranched oligomer may be composed of two units derived from branching agents (X) linked by a structure of Formula XI with branches of Formula IX, or a hyperbranched oligomer may be composed of three or four branching agents linked by structures of Formulae XI and XIII with branches of structure Formula IX. Of course as discussed above, any combination of Formulae are possible and could be present in a single reactive hyperbranched oligomer.

An exemplary representation of a reactive hyperbranched oligomer of the invention is provided below:

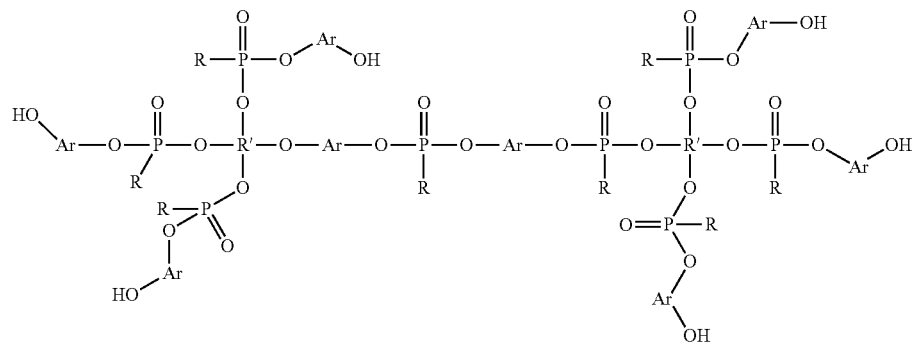

where Ar is an aryl or heteroaryl group, R is a $C_1$-$C_4$ alkyl group or an aryl group, and R' is an alkyl or aromatic group derived from a branching agent.

In some embodiments, the molecular weight (weight average molecular weight as determined by gel permeation chromatography based on polystyrene calibration) range of the hyperbranched oligophosphonates, random or block co-oligo(phosphonate ester)s, and co-oligo(phosphonate carbonate)s may be from about 500 g/mole to about 18,000 g/mole or any value within this range. In other embodiments, the molecular weight range may be from about 1500 g/mole to about 15,000 g/mole, about 3000 g/mole to about 10,000 g/mole, or any value within these ranges. In still other embodiments, the molecular weight range may be from about 700 g/mole to about 9000 g/mole, about 1000 g/mole to about 8000 g/mole, about 3000 g/mole to about 4000 g/mole, or any value within these ranges.

The phosphonate and carbonate content of the hyperbranched oligomeric phosphonates, random or block co-oligo(phosphonate carbonate)s, and co-oligo(phosphonate ester)s may vary among embodiments, and embodiments are not limited by the phosphonate and/or carbonate content or range of phosphonate and/or carbonate content. For example, in some embodiments, the co-oligo(phosphonate carbonate)s or co-oligo(phosphonate ester)s may have a phosphorus content, of from about 2% to about 12% by weight, 2% to about 10% by weight, or less than 10% by weight of the total oligomer.

The reactive hyperbranched oligomers of various embodiments may have greater than about 40% or greater than about 50% reactive end groups based on the total number of branch terminations as determined by known titration methods. In certain embodiments, the reactive hyperbranched oligomers may have greater than about 75% or greater than 90% of the reactive end groups based on the total number of branch terminations as determined by titration methods. In further embodiments, the reactive hyperbranched oligomers may have from about 40% to about 98% reactive end groups, about 50% to about 95% reactive end groups, or from about 60% to about 90% end groups based on the total number of branch terminations. As discussed above individual branch terminations may have more than one reactive end group. Therefore, in some embodiments, the reactive hyperbranched oligomers may have greater than 100% reactive end groups. As discussed above, the term "reactive end groups" is used to describe any chemical moiety at a branch termination that is capable of reacting with another chemical moiety. A large number of reactive functional groups are known in the art and encompassed by the invention. In particular embodiments, the reactive end groups may be hydroxyl, epoxy, vinyl, or isocyanate groups.

Without wishing to be bound by theory, due to their hyperbranched nature, the reactive hyperbranched oligomers of the invention may exhibit low melt viscosities when sheared as compared to linear oligomeric phosphonates. Thus, the reactive hyperbranched oligomers described herein can be blended with monomers, oligomers, and polymers without diminishing melt processability. The hyperbranched oligophosphonates of various embodiments, therefore, can provide better meltability and improved processing. In addition, the reactive hyperbranched oligomers of the invention may be of higher molecular weight and provide greater reactivity increasing the crosslinking and improving the toughness of polymer compositions over similar compositions prepared using linear oligomeric phosphonates. In some embodiments, the reactive hyperbranched oligomers of the invention may be used as reactive or non-reactive additives in thermoplastics to improve shear thinning. For example, hyperbranched oligomers may be prepared that have no or very few reactive end groups that can be used to improve shear thinning without reacting, or crosslinking, the polymer to which the oligomers are added.

The oligomeric phosphonates of various embodiments including linear and hyperbranched oligophosphonates can exhibit a high molecular weight and/or a narrow molecular weight distribution (i.e., low polydispersity). For example, in some embodiments, the oligomeric phosphonates may have a weight average molecular weight (Mw) of about 1,000 g/mole to about 18,000 g/mole as determined by $\eta_{rel}$ or GPC, and in other embodiments, the oligomeric phosphonates may have a Mw of from about 1,000 to about 15,000 g/mole as determined by $\eta_{rel}$ or GPC. The number average molecular weight (Mn), in such embodiments, may be from about 1,000 g/mole to about 10,000 g/mole, or from about 1,000 g/mole to about 5,000 g/mole, and in certain embodiments the Mn may be greater than about 1,200 g/mole. The narrow molecular weight distribution (i.e., Mw/Mn) of such oligomeric phosphonates may be from about 1 to about 7 in some embodiments and from about 1 to about 5 in other embodiments. In still other embodiments, the co-oligo(phosphonate carbonate)s may have a relative viscosity ($\eta_{rel}$) of from about 1.01 to about 1.20. Without wishing to be bound by theory, the relatively high molecular weight and narrow molecular weight distribution of the oligomeric phosphonates of the invention may impart a superior combination of properties. For example, the oligomeric phosphonates of embodiments are extremely flame retardant and exhibit superior hydrolytic stability and can impart such characteristics on a polymer combined with the oligomeric phosphonates to produce polymer compositions such as those described below. In addition, the oligomeric phosphonates of embodiments, generally, exhibit an excellent combination of processing characteristics including, for example, good thermal and mechanical properties.

Some embodiments are directed to methods for making the oligomeric phosphonate of the invention. Linear oligomers such as those described above may generally be prepared by the methods described in U.S. Pat. Nos. 6,861,499, 7,816,486, 7,645,850, and 7,838,604 and U.S. Publication No. 2009/0032770, which are incorporated by reference above. In some embodiments, the polymerization time may be reduced to reduce the number of monomeric units incorporated into the oligomer. In other embodiments, a molar excess of a monomeric unit having hydroxyl functional groups such as, for example, aromatic dihydroxy compounds, dihydric phenols, or bisphenols, may be provided in the reaction mixture to increase likelihood that both termini of the linear oligomer contain hydroxyl end groups.

Other embodiments are directed to methods for making reactive hyperbranched oligomers. For example, in various embodiments, reactive hyperbranched oligomers can be prepared by providing mixtures of monomers, such as, for example, a phosphonate and a co-monomer, in the case of co-oligo(phosphonate carbonate)s, a phosphonate, a co-monomer, and carbonate monomer or oligomer, or in the case of co-oligo(phosphonate ester)s, the phosphonate and a co-monomer can be combined with an ester monomer or oligomer. The reaction mixture may include a monomer mixture, such as those described above, a branching agent, a catalyst, and various solvents and co-reagent. In some embodiments, such methods may include the step of heating the reaction mixture, and in other embodiments, the method may include applying a vacuum to the reaction mixture during heating to remove volatile by-products of the reaction.

In certain embodiments, the components of the monomer mixture may vary among embodiments and may depend on the type of oligomer or co-oligomer to be synthesized. For example, certain embodiments include phosphonate monomers such as phosphonic acid diaryl esters or diaryl phosphonates. Such phosphonate monomers may have any structure, and in some embodiments, may be of general Formula XIV:

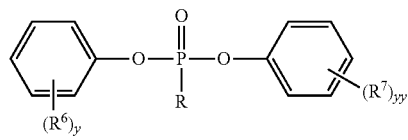

XIV where each $R^6$ and each $R^7$ can independently be a hydrogen, $C_1$-$C_4$ alkyl, each y and yy are, independently integers, of 1 to 5, and R can be $C_{1-20}$ alkyl, $C_{2-20}$ alkene, $C_{2-20}$ alkyne, $C_{5-20}$ cycloalkyl, or $C_{6-20}$ aryl. In some embodiments, the phosphonic acid diaryl ester may be diphenyl methylphosphonate (DPP) or methyldiphenoxyphosphine oxide.

Without wishing to be bound by theory, the use of high purity diaryl alkylphosphonate or optionally substituted diaryl alkylphosphonate, and in particular embodiments, high purity DPP, in the preparation of the oligomeric phosphonates of the invention may provide improved properties over similar polymers or oligomers described in the prior art. The term "high purity" with reference to diaryl alkylphosphonate or optionally substituted diaryl alkylphosphonate and DPP describes a total acidic components of less than about 0.15% by weight, less than about 0.10% by weight, and in certain embodiments, less than about 0.05% by weight. Such acidic components are known in the art and may include, but are not limited to, phosphoric acid, phosphonic acid, methyl phosphonic acid, and methyl phosphonic acid mono phenylester. Because the diaryl alkylphosphonate, optionally substituted diaryl alkylphosphonate, or DPP used in the preparation of the random copolymers of the invention include low levels of such acidic components, the oligomeric phosphonates produced using these high purity phosphonate monomers may include significantly reduced levels of the acidic component contaminants. In some embodiments, the oligomeric phosphonates of embodiments may include substantially no acidic component contaminants, and in other embodiments, the oligomeric phosphonates of embodiments may include, for example, total acidic components of less than about 0.15% by weight, less than about 0.10% by weight, and in certain embodiments, less than about 0.05% by weight.

The co-monomer may be any monomer, oligomer or polymer capable of reacting with the phosphonate monomers described above in a polymerization reaction. For example, in some embodiments, the co-monomer may be an aromatic dihydroxy compound, a dihydric phenol, a bisphenol, and the like or combinations thereof. Particular examples of such compounds include, but are not limited to, resorcinols, hydroquinones, and bisphenols, such as bisphenol A, bisphenol F, and 4,4'-biphenol, phenolphthalein, 4,4'-thiodiphenol, 4,4'-sulfonyldiphenol, 3,3,5-trimethylcyclohexyldiphenol. Any such compounds or combination of such compounds can be used in the methods of embodiments.

In embodiments that include a carbonate monomer, the carbonate monomer may be any difunctional carbonate known in the art, or combinations thereof. In some embodiments, the carbonate monomer may be a diaryl carbonate monomer such as, but not limited to, diphenyl carbonate, 4-tert-butylphenyl-phenyl carbonate, di-(4-tert-butylphenyl) carbonate, biphenyl-4-yl-phenyl carbonate, di-(biphenyl-4-yl)carbonate, 4-(1-methyl-1-phenylethyl)-phenyl-phenyl carbonate, di-[4-(1-methyl-1-phenylethyl)-phenyl]carbonate, and the like and combinations thereof. In certain embodiments, the carbonate monomer may be diphenyl carbonate.

The branching agent used in the methods of various embodiments may vary and can be included as a separate component or can be generated in situ by action of the polymerization catalyst with a dihydroxy compound. For example, in situ branching agents can be formed from dihydroxy compounds by splitting or Fries rearrangements. Without wishing to be bound by theory, a portion of bisphenol A in reaction mixtures such as those described above can spontaneously undergo a reaction that increases the number of reactive hydroxyl groups extending from the bisphenol A molecule and such bisphenol A molecules can function as branching agents. Bisphenol A and other similar aromatic dihydroxy compounds can be termed "splitable" dihydroxy compounds because they can undergo these reactions to form branching species in situ under polycondensation conditions.

In some embodiments, the branching agent may be polyfunctional acids, polyfunctional glycols, or acid/glycol hybrids. In other embodiments, the hyperbranched oligomeric phosphonates may have units derived from tri or tetrahydroxy aromatic compounds or triaryl or tetraaryl phosphoric acid esters, triaryl or tetraaryl carbonate or triaryl or tetraaryl esters or combinations thereof such as, but not limited to, trimesic acid, pyromellitic acid, trimellitic anhydride, pyromellitic anhydride, trimethylolpropane, dimethyl hydroxyl terephthalate, pentaerythritol, and the like and combinations thereof. Such branching agents provide branch points within the hyperbranched oligomeric phosphonate.

In particular embodiments, the branching agent may be a triaryl phosphate such as, for example, those of Formula VIII:

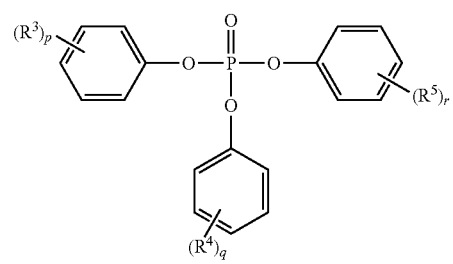

VIII where each $R^3$, $R^4$, and $R^5$ can, independently, be a hydrogen, $C_1$-$C_4$ alkyl of, and each of p, q, and r are independently integers of from 1 to 5. In various embodiments, the branching agent may be 1,1,1-tris(4-hydroxyphenyl)ethane, phosphoric triaryl esters, tri and tetra functional carbonates or esters, and the like and combinations thereof, and in certain exemplary embodiments, the branching agent may be triphenyl phosphate. In certain embodiments, trihydroxy and tetrahydroxy compounds used for preparing oligomeric phosphonates of embodiments can include, but are not limited to, phloroglucinol, 4,6-dimethyl-2,4,6-tri-(4-hydroxy phenyl)-2-heptene, 4,6-dimethyl-2,4,6-tri-(4-hydroxy phenyl)-heptane, 1,3,5-tri-(4-hydroxy phenyl)-benzene, 1,1,1-tri-(4-hydroxy phenyl)-ethane, tri-(4-hydroxy phenyl)-phenyl methane, 2,2-bis-[4,4-bis-(4-hydroxy phenyl)-cyclohexyl]-propane, 2,4-bis-(4-hydroxy phenyl)isopropyl phenol, 2,6-bis-(2'-hydroxy-5'-methyl benzyl)-4-methyl phenol 2-(4-hydroxy phenyl)-2-(2,4-dihydroxy phenol)-propane, tetra-(4- hydroxy phenyl)methane, tetra-[4-(4-hydroxy phenyl isopropyl)phenoxy]-methane, 1,4-bis-(4,4"-dihydroxy triphenyl methyl)-benzene, and the like and combinations and mixtures thereof.

The amount of branching agent added to the reaction, whether the branching agent was combined with the other monomers prior to heating, added after heating has begun, or both, may be similar and can vary among embodiments. In various embodiments, the branching agent may be provided in an amount from about 0.5 mole % or about 1 mole % up to about 10 mole % or greater. For example, in some embodiments, the total branching agent provided may be 1 mole % or greater, 2 mole % or greater, 3 mole % or greater, 4 mole % or greater, 5 mole % or greater, 6 mole % or greater, 7 mole % or greater, 8 mole % or greater, 9 mole % or greater, or 10 mole % or greater. In some embodiments, a co-monomer such as an aromatic dihydroxy compound, dihydric phenol, bisphenol, or combination thereof may be provided in the monomer mixture in a molar excess over the total of the phosphonate monomer and branching agent, and in embodiments including a carbonate component, the phosphonate monomer, branching agent, and carbonate monomer. Without wishing to be bound by theory, a molar excess of dihydroxy compound may increase the number of hydroxyl terminations in the reactive hyperbranched oligomers of the invention allowing for the production of oligomers that have predominately hydroxyl terminations.

The methods of embodiments generally may require a catalyst, and any catalyst known in the art useful for facilitating transesterification or condensation may be used in connection with the methods described herein. For example, in some embodiments, the oligomerization catalyst may include a mixture of catalysts and in some cases, a co-catalyst. In some embodiments, the catalyst may be an alkaline, alkaline earth, or other metal metal catalyst such as, but not limited to, sodium phenolate.

In other embodiments, catalysts useful in the methods of the invention may not contain an alkaline, alkaline earth, or other metal cation. Such catalysts can be removed by heating during the condensation reaction with other volatile components by evaporation, sublimation, or thermal decomposition. Because the material produced contains no metal, an additional advantage of the reactive hyperbranched oligomers may be improved hydrolytic stability. In particular embodiments, such oligomerization catalysts may be of Formula XV:

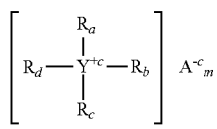

XV where Y can be nitrogen, phosphorous, or arsenic, +c represents the charge associated with Y, $R_a$, $R_b$, $R_c$ and $R_d$ can independently be phenyl, tert-butyl, methyl, ethyl, propyl, butyl, or other groups provided that the catalyst acts as an oligomerization catalyst, and A is a counter anion such as, but is not limited to, phenolate, acetate, borohydrides, halogen, hydroxide, propionate, formate, butyrate and the like and −c is the charge associated with the A. In some embodiments, Y is phosphorous, $R_a$, $R_b$, $R_c$, and $R_d$ are phenyl, and the anion is phenolate or acetate. In certain embodiments, the catalyst may be a phosphonium catalyst such as, for example, tetraphenylphosphonium catalyst or its derivatives and associated anion such as tetraaryl borohydride, a halide, and a substituted or unsubstituted phenolate group. In particular embodiments, the catalyst may be tetraphenylphosphonium phenolate.

The oligomerization catalyst may be added in any form. For example, the catalyst may be added to a reaction mixture or monomer mixture as a solid, such as a powder, dissolved in a solvent, or as a melt. Such catalysts may be provided in any amount necessary to promote oligomerization, and the amount of catalyst may be used to control the rate of reaction and control molecular weight. The skilled artisan can determine an appropriate amount of catalyst used in the methods embodied herein. In certain embodiments, the molar amount of a catalyst used, relative to the molar amount of co-monomer, or bisphenol, can be from about 0.00004 moles to about 0.0012 moles per one mole of co-monomer. Where an increase in molecular weight of a oligophosphonate is desired the amount of catalyst, a catalyst with a lower vapor pressure, or a lower pressure of the vessel may be used to increase molecular weight.

In some embodiments, the reaction may further include one or more co-catalysts, which can be provided in addition to the one or more catalyst to increase the rate of the oligomerization. Such co-catalysts may be, for example, salts of alkali metal salts and alkaline earth metal salts such as, for example, hydroxides, alkoxides, and aryl oxides of lithium, sodium, and potassium. In certain embodiments, the alkali metal salt may be a hydroxide, alkoxide, or aryl oxide salt of sodium, and in some embodiments, the co-catalyst may be sodium hydroxide and sodium phenolate. The amount of the co-catalyst provided may vary and may be, for example, from about 1 µg/kg to about 200 µg/kg, 5 µg/kg to 150 µg/kg, and, in certain embodiments, about 10 µg/kg to about 125 µg/kg, based in each case on the mass of aromatic dihydroxide used calculated in each case as sodium. In certain embodiments, the oligomeric phoshonates of the invention may be prepared without co-catalysts.

In general, the methods described herein include a heating step in which a reaction mixture including phosphonate monomers, co-monomers, and a catalyst are heated to a suitable reaction temperature. In such embodiments, the reaction mixture may be heated to a temperature at which the components of the reaction mixture melt and undergoes oligomerization as the melted components of the reaction mixture are stirred. The reaction is, therefore, carried out "in a melt." In some embodiments, the reaction temperature may be from about 100° C. to about 350° C., and in other embodiments, the reaction temperature may be from about 200° C. to about 310° C. In further embodiments, the temperature may be changed during the reaction within the ranges provided above without limitation.

In various embodiments, the oligomerization methods of the invention may be carried out under a reduced pressure, and in some embodiments, the reaction mixture may be purge. The pressure of the reaction vessel is, generally, chosen to aid in the removal of volatile reaction products, excess reagents, and volatile oligomerization catalysts such as the phosphonium catalyst described above from the reaction vessel during oligomerization. In certain embodiments, the pressure may be selected to allow for the removal volatile compounds, such as phenol generated by the reaction and heating. Without limitation, the pressure may range from above atmospheric pressure to below atmospheric pressure, and the person of ordinary skill in the art can determine an appropriate pressure to achieve this effect based on the components of the reaction mixture. In more specific exemplary embodiments, the pressure from about 760 mm Hg to about 0.05 mm Hg, about 500 mm Hg to about 0.1 mm Hg, or about 400 mm Hg to about 0.3 mm Hg in the reaction vessel at any time during the reaction.

Generally, the reaction is completed when excess reagents and volatile reaction products are removed from the vessel in an amount to provide an oligomeric phosphonate having the desired transparency, $T_g$, $M_w$, relative viscosity, and polydispersity for the intended use. The reaction time may depend upon a number of factors including, but not limited to, the reaction temperature, concentration of components, total volume of the reaction mixture, rate of removal of reactants from the vessel, the addition of catalyst, the inclusion of various heating steps, and the like, and combinations thereof. During the oligomerization, volatile compounds such as phenol are evolved and can be distilled off at elevated temperature, under reduced pressure and/or purge with inert gas. The reaction may be continued until the required degree of condensation is reached, and in some embodiments, the degree of condensation can be determined based on a decrease or cessation of the evolution of volatile compounds. In some embodiments, the reaction time may be less than about 10 hours. For example, in various embodiments, the reaction time may be from about 3 hours to about 8 hours, about 4 hours to about 6 hours, or any time there between.

Various embodiments are directed to methods in which oligomerization is carried out "in a melt" under conditions necessary for "melt oligomerization." The reaction conditions for melt oligomerization are not particularly limited, and melt oligomerization can be conducted in a wide range of operating conditions. In particular embodiments, melt oligomerization may refer to the conditions necessary to effect reaction between the diaryl alkyl phosphonate, or diaryl alkyl phosphonate combined with a diaryl carbonate, a diaryl ester or oligomers thereof, and one or more dihydroxy aromatic co-monomer with a volatile transesterification catalyst. In general, such reactions can be carried out in a moisture and oxygen-free atmosphere under reduced pressure and/or a purge of an inert gas such as, for example, nitrogen or argon. The temperature of the reaction vessel for such melt oligomerization methods may be from about 100° C. to 350° C. or, in certain embodiments, from 200° C. to 310° C.

In some embodiments, melt oligomerization may be carried out in one or more stages such as those described above, and in particular embodiments, the oligomerization stages may include the addition of additional oligomerization catalysts. For example in some embodiments, a oligomerization catalyst and/or co-catalysts may be added to the reaction mixture melt together in a stage, and in other embodiments, a oligomerization catalyst may be added to a reaction mixture in one stage and a co-catalyst may be added to the reaction mixture in a different stage. In still other embodiments, a oligomerization catalyst may be added in a continuous or semi-continuous manner to the reaction mixture where one or more stages of the process are combined to form a continuous process. Thus, embodiments include preparation of oligomeric phosphonates, random or block co-oligo(phosphonate ester)s and co-oligo(phosphonate carbonate)s and hyperbranched oligomeric phosphonates, random or block co-oligo(phosphonate ester)s and co-oligo(phosphonate carbonate)s in batch or continuous flow processes.

In still other embodiments, co-oligo(phosphonate ester)s and co-oligo(phosphonate carbonate)s may be prepared by combining phosphonic acid diaryl ester, diaryl carbonate or diaryl ester monomers, and the aromatic dihydroxy co-monomer with catalyst to create a reaction mixture and heating this mixture. A branching agent can be added or additional branching agent can be added during the heating step while the monomers are oligomerizing. In further embodiments, such methods may be carried out in the absence of a branching agent to provide oligomeric phosphonates, random co-oligo(phosphonate ester)s and co-oligo(phosphonate carbonate)s, and block co-oligo(phosphonate ester)s and co-oligo(phosphonate carbonate)s that are substantially unbranched.

In general, the heating may be stopped when volatile by-products of the reaction such as phenol are no longer evolved from the reaction; however, in some embodiments, a second heating step may be employed after the evolution of volatile by-products has stopped. This second heating step may provide a devolatilization step in which residual monomers, and in certain embodiments, residual co-monomer, and remaining volatile by-products are removed without increasing the molecular weight of the oligophosphonates, co-oligo(phosphonate ester)s, or co-oligo(phosphonate carbonate)s.

Certain embodiments include methods, in which the end group of a predominately hydroxyl terminated oligomeric phosphonate is reacted to change the composition of the end group. For example, in some embodiments, a hyperbranched predominately hydroxyl terminated oligomeric phosphonate may be converted to a hyperbranched epoxy terminated oligomeric phosphonate by combining the hyperbranched predominately hydroxyl terminated oligomeric phosphonate with an effective amount of epichlorohydrin. This mixture may be reacted for a time period sufficient to allow the reaction of the epichlorohydrin with the hydroxyl termini to produce an epoxy termini as illustrated below:

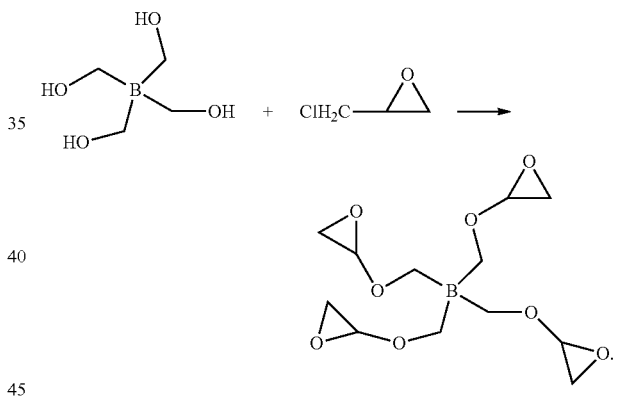

where B represents the hyperbranched oligomer which may be an oligophosphonate, random or block co-oligo(phosphonate ester)s or co-oligo(phosphonate carbonate)s having a hydroxyl termini. While four hydroxyl termini are illustrated for simplicity, the hyperbranched oligomer of various embodiments may include any number of branches. The epoxy terminated hyperbranched oligomer produced by such methods can be reacted with a variety of chemical functionalities present on monomers, oligomers or polymers such as alcohols, organic carboxylic acids and salts, anhydrides, acyl chlorides, aldehydes, ketones, amines, thiols, Grignard reagents, water, sodium hydroxide inorganic acids and salts.

In some embodiments, the pressure and the temperature may be adjusted during the oligomerization reaction to create two or more stages during the course of the reaction, and in certain, embodiments, reactants or oligomerization catalysts may be added to the reaction mixture during one or more of such stages. For example, in some embodiments, the reaction may have at least two stages; a first stage that is carried out until generation of volatile compounds has stopped or is significantly reduced, and a second, post reaction, stage in which generation of volatile compounds is minimal. In such embodiments, the first stage may be from about 1 hours to about 6 hours, and the second stage may be from about 1 hours to about 6 hours, the reaction temperature of the first and second stage may, independently, be from about 100° C. to about 350° C., and both the first and second stages may be carried out at reduced pressure. Without wishing to be bound by theory, methods that include a second stage may produce oligomeric phosphonates having hydrolytic stability that is better than methods having only one stage.

In other embodiments, the methods may be composed of more than one or more than two stages. For example, in some embodiments the reaction temperature may be increased incrementally while the volatile compounds are generated, to control the rate of reaction, the rate of evolution of volatile compounds, and/or the pressure in the reaction vessel. In each individual step, the pressure, the temperature or both the temperature and pressure may be increased or decreased. For example, in some embodiments, the temperature may be increased in a first step while the pressure is held constant, and the pressure may be increased in a second step while the temperature remains constant. In a third step, the temperature may be increased and the pressure may be decreased simultaneously, and the temperature may be decreased and the pressure may be increased simultaneously in a fourth step. Embodiments may further include a step in which the temperature and pressure within the vessel are maintained. Such steps may be combined in any order, and in other exemplary embodiments additional similar steps may be incorporated into the methods of embodiments. The number of reaction steps, or stages, is not limited, and in various embodiments, the number of reaction steps may be from 2 to 10, from 3 to 8, and in certain embodiments, from 5 to 7 and any number between these ranges.

In some exemplary embodiments, the reaction temperature for each step of the method may be from about 150° C. to about 400° C., and in other embodiments, the reaction temperature for each step of the method may be from about 180° C. to about 330° C. In such embodiments, the residence time for each step may be from about 15 minutes to about 6 hours, and pressure for each step may be from about 250 mbar to about 0.01 mbar. In some embodiments, the reaction temperature may increase from one step to the other and the pressure may decrease from one step to the next.

For example, in some embodiments, transesterification reaction of the aromatic dihydroxide, diaryl carbonate, diaryl alkylphosphonate and at least one catalyst in the melt is preferably carried out in a two-step process. In the first stage, the melting of the aromatic dihydroxide, diaryl carbonate, and diaryl alkylphosphonate may be carried out at a temperature of from about 80° C. to about 250° C., about 100° C. to about 230° C., and, in certain embodiments, from about 120° C. to about 190° C. The first stage may be carried out under atmospheric pressure and may be carried out for from about 0 hours to about 5 hours and, in some embodiments, from about 0.25 hour to about 3 hours. After melting, a catalyst may be added to the melt, and co-oligo(phosphonate carbonate)s may be prepared from the aromatic dihydroxide, diaryl carbonate and diaryl alkylphosphonate by applying a vacuum (up to about 2 mmHg), increasing the temperature (up to about 260° C.), and distilling off monophenol produced as a by-product of the condensation. The co-oligo(phosphonate carbonate) thus prepared may have an average molecular weight Mw (determined by measuring the relative solution viscosity in dichloromethane or in mixtures of equal amounts by weight of phenol/o-dichlorophenol, calibrated by light scattering) in the range of from about 1000 to about 18,000, and in some embodiments, from about 1,000 to about 11,000. In such embodiments, up to about 80% of the monophenol can be recovered from the process.

In a second stage, the reaction temperature may be increased to from about 250° C. to 320° C. or about 270° C. to about 295° C., and the pressure may be reduced to less than about 2 mmHg. Additional by-product monophenols may be recovered in the second step. The amount of monophenol produced in the second step may be less than the amount of monophenol produced in the first step as the monophenol are a result loss of end groups in the co-oligo(phosphonate carbonate)s in the reaction. For example, the amount of monophenol produced may be less than about 5%, less than about 2%, or less than about 1% of the amount of monophenol produced in the first step.

The monophenols eliminated during transesterification of the aromatic dihydroxide, diaryl carbonate, diaryl alkylphosphonate in the production of oligomeric phosphonates of the invention may be purified and isolated, prior to the use in the diaryl carbonate synthesis. The crude monophenols isolated during transesterification may be contaminated, inter alia, with diaryl carbonates, diaryl alkylphosphonate, aromatic dihydroxide, salicylic acid, isopropenylphenol, phenyl phenoxybenzoate, xanthone, hydroxymonoaryl carbonate, and the like depending on transesterification conditions and distillation conditions. The purification can be effected by the customary purification processes, e.g., distillation or recrystallization. The purity of the monophenols following purification may be greater than 99%, greater than 99.8%, or greater than 99.95%.

Methods for making the oligomeric phosphonates of the invention can be conducted as a batch, semibatch, or a continuous process. The structure of reactors used in such methods is not particularly limited so long as the reactor has an ordinary capability of stirring, heating, reduced pressure, and includes ports for addition and removal of reagents, solvents, removable catalyst, and/or or reaction by-products. Such reactors can be equipped, for example, with a temperature controlled condenser or cold finger, for the selective removal of by-product hydroxy aromatic compounds or phenol derived compounds generated during oligomerization.

The methods of various embodiments may be carried out in, for example, stirred tanks, thin-film evaporators, falling-film evaporators, stirred tank cascades, extruders, kneaders, simple disc reactors, disc reactors for high viscosity substances, and combinations thereof. The devices, apparatuses and reactors suitable for the individual reaction evaporator stages may depend on the course of the process and may include, but are not limited to, heat exchangers, flash apparatuses, separators, columns, evaporators, stirred containers, reactors, and any other commercially available apparatuses which provide the necessary residence time at selected temperatures and pressures. The chosen devices must permit the necessary heat input and must be designed so that they are suitable for the continuously increasing melt viscosity. The various devices may be connected to one another via pumps, pipelines, valves, and the like, and combinations thereof. The pipelines between all facilities are preferably as short as possible and the number of bends in the pipes kept as small as possible in order to avoid unnecessarily prolonging residence times.

Other embodiments of the invention are directed to oligomer compositions including at least one oligophosphonate, random or block co-oligo(phosphonate ester) and co-oligo (phosphonate carbonate) and hyperbranched oligophosphonate, random or block co-oligo(phosphonate ester) and co-oligo(phosphonate carbonate) and at least one polymer or second oligomer or monomer. Such compositions including an oligomeric phosphonate and a polymer or second oligomer or monomer are referred to herein as "polymer compositions." The at least one polymer or second oligomer or monomer may be any commodity or engineering plastic, and such polymer compositions can be produced by blending, mixing, or compounding the constituent polymers and oligomers. "Engineering plastics" as used herein include, both thermoplastics and thermosetting resins and may include, but are not limited to, polycarbonates, epoxies derived polymers, polyepoxies (e.g., polymers resulting from the reaction of one or more epoxy monomer or oligomer with one or more chain extender or curing agent such as a mono or multifunctional phenol, amine, benzoxazine, anhydride or combination thereof), benzoxazines, polyacrylates, polyacrylonitriles, polyesters, such as, poly(ethylene terephthalate), poly(trimethylene terephthalate), and poly(butylene terephthalate)], unsaturated polyesters, polyamides, polystyrenes including high impact strength polystyrene, polyureas, polyurethanes, polyphosphonates, polyphosphates, poly(acrylonitrile butadiene styrene)s, polyimides, polyarylates, poly(arylene ether) s, polyethylenes, polypropylenes, polyphenylene sulfides, poly(vinyl ester)s, polyvinyl chlorides, bismaleimide polymers, polyanhydrides, liquid crystalline polymers, cellulose polymers, or any combination thereof. The polymer or second oligomer may, therefore, include, or partially include one or more polycarbonate, polyacrylate, polyacrylonitrile, polyester, polyamide, polystyrene, polyurethane, polyepoxy, poly(acrylonitrile butadiene styrene), polyimide, polyarylate, poly(arylene ether), polyethylene, polypropylene, polyphenylene sulfide, poly(vinyl ester), polyvinyl chloride, bismaleimide polymer, polyanhydride, liquid crystalline polymer, polyether, polyphenylene oxide, cellulose polymer, benzoxazine, a hydrolytically stable polyphosphonate, and the like and combinations of these. In some embodiments, the polymer or second oligomer or monomer may contain functional groups that are capable of chemically reacting with the end groups of the oligomeric phosphonates of embodiments, and in certain embodiments in which the oligomeric phosphonates include predominately hydroxyl or epoxy or vinyl termini, the polymer or second oligomer may contain functional groups capable of reacting with hydroxyl or epoxy or vinyl end groups.

Due to the structure and properties of the oligomeric phosphonates of embodiments, the polymer compositions described herein may exhibit exceptional flame resistance and good melt processing characteristics. For example, in general, polymer compositions of the invention may exhibit a limiting oxygen index (LOI) of at least about 27. The oligomeric phosphonates of the invention further provide flame resistance and dimensional stability while maintaining high heat deflection temperature (HDT) near that of the unmodified engineering polymers.

In some embodiments, the oligomeric phosphonates of the invention may be combined with a prepolymer mixture composed of components selected to create a polymer such as those described above under conditions appropriate for polymerization. For example, in various embodiments, a oligomeric phosphonate such as those described above may be combined with a prepolymer mixture including monomers for creating polycarbonate, polyacrylate, polyacrylonitrile, polyester, polyamide, polystyrene, polyurethane, polyurea, polyepoxy, poly(acrylonitrile butadiene styrene), polyimide, polyarylate, poly(arylene ether), polyethylene, polypropylene, polyphenylene sulfide, poly(vinyl ester), polyvinyl chloride, bismaleimide polymer, polyanhydride, liquid crystalline polymer, polyether, polyphenylene oxide, cellulose polymer, benzoxazine, a hydrolytically stable polyphosphonate, and the like, and this mixture may be heated and mixed until a viscous polymer is formed, or in other embodiments, a curing agent may be provided to the mixture and mixing may continue until a cured polymer is formed.

In particular embodiments, the polymer combined with the oligomeric phosphonates of the invention may be an epoxy resin. For example, in some embodiments, an oligomeric phosphonate, and in particular, hyperbranched oligomeric phosphonates may be combined with an epoxy resin or a prepolymer or mixture of appropriate monomers to produce an epoxy resin. Any epoxy resin can be used in such embodiments, and in certain embodiments, the resin may contain glycidyl groups, alicyclic epoxy groups, oxirane groups, ethoxyline groups, or similar epoxy groups or combinations thereof that can react with hydroxyl or epoxy resins associated with the oligomeric phosphonates. Such epoxy resins are well known in the art and include, but are not limited to, novolac-type epoxy resin, cresol-novolac epoxy resin, triphenolalkane-type epoxy resin, aralkyl-type epoxy resin, aralkyl-type epoxy resin having a biphenyl skeleton, biphenyl-type epoxy resin, dicyclopentadiene-type epoxy resin, heterocyclic-type epoxy resin, epoxy resin containing a naphthalene ring, a bisphenol-A type epoxy compound, a bisphenol-F type epoxy compound, stilbene-type epoxy resin, trimethylol-propane type epoxy resin, terpene-modified epoxy resin, linear aliphatic epoxy resin obtained by oxidizing olefin bonds with peracetic acid or a similar peracid, alicyclic epoxy resin, or sulfur-containing epoxy resin. In some embodiments, the epoxy resin may be composed of two or more epoxy resins of any of the aforementioned types. In particular embodiments, the epoxy resins may be aralkyl-type epoxy resins, such as epoxy resins derived from bisphenol A or methylene dianiline. The epoxy may also contain one or more additional components such as, for example, a benzoxazine compound or resin, and in some embodiments, the oligomeric phosphonate may be used as epoxy modifiers, crosslinkers for epoxy resins, or epoxy hardeners in such epoxy resin polymer compositions.

In some embodiments the polymer compositions described here may further include additional components fillers, fibers, such as, but not limited to, chopped or continuous glass fiber, metal fibers, aramid fibers, carbon fibers, or ceramic fibers, surfactants, organic binders, polymeric binders, crosslinking agents, diluents, coupling agents, flame retardant agents, anti-dripping agents such as fluorinated polyolefins, silicones, and, lubricants, mould release agents such as pentaerythritol tetrastearate, nucleating agents, anti-static agents such as conductive blacks, carbon nanotubes, and organic antistatics such as polyalkylene ethers, alkylsulfonates, perfluor sulfonic acid, perfluorbutane sulfinic acid potassium salt, and polyamide-containing polymers, catalysts, colorants, inks, dyes, antioxidants, stabilizers, and the like and any combinations thereof. In such embodiments, the one or more additional components or additives may make up from about 0.001 wt. % to about 1 wt. %, about 0.005 wt. % to about 0.9 wt. %, about 0.005 wt. % to about 0.8 wt. %, about 0.04 wt. % to about 0.8 wt. %, and in particular embodiments, from about 0.04 wt. % to about 0.6 wt. % based on the total composition. In other embodiments, additional components such as glass fiber or other fillers may be provided at much higher concentrations up to 70 volume (vol.) %. For example, in some embodiments the oligomeric phosphonates polymer compositions may include up to about 70 vol. % glass fiber, and in other embodiments, the oligomeric polymer compositions may include from about 5 vol. % to about 70 vol. %, from about 10 vol. % to about 60 vol. %, or about 20 vol. % to about 50 vol. % glass fiber.

Polymer compositions including oligomeric phosphonates and other engineering polymers and/or additional components or additives can be prepared by conventional means. For example, in some embodiments, the respective constituents can be mixed in a known manner and subjected to melt compounding and/or melt extrusion at temperatures of about 200° C. to about 400° C. in customary aggregates such as internal kneaders, extruders, or twin-screw apparatuses. Mixing the individual constituents can be affected either successively or simultaneously and either at about room temperature (about 20° C.) or at higher temperature. For example, in some embodiments, the engineering plastic and/or all additional components or additives can be introduced into the oligomeric phosphonates, by compounding. In other embodiments, the individual constituents can be introduced separately in different stages of the preparation process into a melt including oligomeric phosphonates. Thus, for example, additives can be introduced during or at the end of the transesterification of aromatic dihydroxides with organic carbonates and diphenylmethyl phosphonate, before or during the formation of oligomeric phosphonates or before or after the polycondensation of the oligomeric phosphonates into a melt.

The form of addition of the compounds according to the invention is not limited. For example, the engineering plastics and/or additional components or additives can be added as solids such as a powder, as concentrate in polycarbonate powder in solution. In industrial embodiments, a side extruder may be operated with a throughput of, for example, 200-1000 kg of oligomeric phosphonate per hour.

The polymer compositions of various embodiments can be used in any application in which a flame retardant polymer is useful. For example, in some embodiments, the polymer compositions of the invention may be used as coatings on plastics, metals, glass, carbon, ceramic, or wood products which can be in a variety of forms, for example as a fiber, molding, laminate, foam, extruded shape or the like, and in other embodiments, the polymer compositions of the invention can be used to fabricate free-standing films, fibers, foams, molded articles, and fiber reinforced composites. Such articles may be well-suited for applications requiring flame resistance. The oligomeric phosphonates of the invention and polymer compositions, including such oligomeric phosphonates, may exhibit outstanding flame resistance and good melt processability making these materials useful in applications for the automotive and electronic sectors that require outstanding fire retardancy, high temperature performance, and melt processability. In addition, these articles may be well suited for a variety of applications as support parts, electrical components, electrical connectors, printed wiring laminated boards, electrical or electromagnetic housings, electrical or electromagnetic subcomponents and components in consumer products that must meet UL or other standardized fire resistance standards.

In some embodiments, the polymer compositions including the oligomeric phosphonates of the invention may be combined with other components or reinforcing materials. For example, in various embodiments, continuous or chopped glass fibers, carbon black or carbon fibers, ceramic particles or fibers, or other organic materials may be included in the polymer compositions of the invention. In particular embodiments, continuous or chopped glass fibers, carbon fibers, ceramic fibers, or other organic materials may be combined with a polymer mixture including an epoxy resin to create a prepreg to prepare laminates. Such laminates may be used to fabricate components such as laminated circuit boards that can be incorporated into articles of manufacture such as electronic goods such as, for example, televisions, computers, laptop computers, printers, cell phones, video games, DVD players, stereos and other consumer electronics.

The oligomeric phosphonates prepared as described above, and polymer compositions including these oligomeric phosphonates are generally self-extinguishing, i.e., they stop burning when removed from a flame and any drops produced by melting in a flame stop burning are almost instantly extinguishes and do not readily propagate fire to any surrounding materials. Moreover, these polymer compositions do not evolve noticeable smoke when a flame is applied.

EXAMPLES

Although the present invention has been described in considerable detail with reference to certain preferred embodiments thereof, other versions are possible. Therefore, the spirit and scope of the appended claims should not be limited to the description and the preferred versions contained within this specification. Various aspects of the present invention will be illustrated with reference to the following non-limiting examples. The following examples are for illustrative purposes only and are not to be construed as limiting the invention in any manner.

Analytical Characterization

The amount of acidic components in diphenyl methylphosphonate (DPP) were determined by gas chromatography (GC) on a non-polar column (Optima 5) by analyzing the sample after derivatization with N-Methyl-N-(trimethylsilyl) trifluoracetamide MSTFA based on the area under the respective GC peaks.

Molecular weight distributions were determined by measuring 0.2% solutions of polymer in tetrahydrofuran by gel permeation chromatography (GPC) with UV detection (at 254 nm). Calibration of the instrument was conducted with linear polystyrene (PS) standards of known molecular weights. The weight average (Mw), number average (Mn) and polydispersity (Mw/Mn), referred to as PD, were evaluated from the chromatograms by using WinGPC software.

End-group analysis was performed using a Bruker Daltonics Reflex III Matrix Assisted Laser Desorption/Ionization Time-of-Flight (MALDI-TOF) instrument. The samples were prepared using dithranol as the matrix material, tetrahydrofuran (THF) as the solvent, and with no exogenous metal cation. The end-groups were determined by analysis of the peak molar mass (m/z) distribution obtained from the spectrum of each sample. Hydroxyl numbers (mg KOH/g) were obtained by titration using the acetylation method. The oligomer sample is dissolved in the acetylating solution (acetic anhydride in dry pyridine). The catalyst (5% N-dimethylaminopyridine in dry pyridine) is then added and allowed to stir for 1 hour. Deionized water is added and stirred for half an hour, before titrating with ethanolic potassium hydroxide to the end-point (change from yellow to blue color). Thymol blue is used as the indicator.

Example 1

Synthesis of Hydroxy-Terminated Oligomers

Phosphonate oligomers with hydroxyl end-groups were synthesized via a two-stage melt condensation process. The first stage was carried out in 12 L stainless steel reactor equipped with a mechanical stirrer and two reflux columns connected in series. To this reactor, 2,2-bis-(4-hydroxyphenyl) propane (BPA, 1800 g, 7.895 mol), diphenyl methylphosphonate (DPP) (1305 g, 5.262 mol), and the catalyst, tetraphenylphosphonium phenolate (TPPP (30% phenol), Example 1 and Example 2. Mw data was obtained using GPC (in THF), calibrated to polystyrene standards. The end-group composition was determined using MALDI-TOF analysis. The amount of chains having reactive hydroxyl groups at both ends of the chain are expressed as bis-OH.

TABLE 1

Comparative Data Ex. 1 and Ex. 2.

| Ex. | Cat.* | Rxn. Time* (min) | Temp.* (° C.) | Vac* (mmHg/min) | Col. Temp.* (° C.) | Tg. (° C.) | Mn/Mw | —OH (%) | —OH mg (KOH/g) |
|---|---|---|---|---|---|---|---|---|---|
| 1 | No | 180 | 250 | <0.5/180 | 200 | 75 | 1000/1800 | 72 | 68 |
| 2 | Yes | 180 | 2 | 1: 10/120<br>2: <0.5/60 | 1: 150<br>2: 200 | 82 | 2200/1200 | 91 | 78 |

*Refers to 2$^{nd}$ stage conditions. First stage conditions were identical.

0.51 g, 0.83 mmol) were added under nitrogen. The monomer/catalyst mixture was heated at 265° C. for hours, with gradual reduction in the vacuum level to 4 mmHg. Both the top and bottom reflux columns were heated to 135° C. After 105 min, the temperature of the bottom column was increased to 150° C. and the top column decreased to 120° C. The phenol by-product was distilled off and collected in a graduated receiving flask. After 5 hours, the product was transferred via a stainless steel bridge to a 6 L stainless steel reactor at 250° C. under nitrogen. The reaction temperature was held at 250° C. for 3 hours under full vacuum (<0.5 mmHg) and the distillation column maintained at 200° C. The product was extruded through the die at the bottom of the reactor into a liquid nitrogen bath and isolated as a coarse white powder. See Table 1 for characterization data.

Example 2

Synthesis of Hydroxy-Terminated Oligomers

Phosphonate oligomers with a high level of termination with bis-hydroxy end-groups (≧90%) were synthesized via a two-stage melt condensation process. The first stage was carried out in a 12 L stainless steel reactor equipped with a mechanical stirrer and two reflux columns connected in series. To this reactor, 2,2-bis-(4-hydroxyphenyl) propane (BPA, 1800 g, 7.895 mol), diphenyl methylphosphonate (DPP) (1305 g, 5.262 mol), and the catalyst, tetraphenylphosphonium phenolate (TPPP (30% phenol), 0.51 g, 0.83 mmol) were added under nitrogen. The monomer/catalyst mixture was heated at 265° C. for 5 hours, with gradual reduction in the vacuum level to 10 mmHg. Both the top and bottom reflux columns were heated to 135° C. After 105 min, the temperature of the bottom column was increased to 150° C., and the top column decreased to 120° C. The phenol by-product was distilled off and collected in a graduated receiving flask. After 5 hours, the product was transferred via a stainless steel bridge to a 6 L stainless steel reactor held at 265° C. under nitrogen. At the start of the second stage, additional catalyst (2.55 g) was added to the reactor. The reaction was held at 265° C./10 mmHg for 2 hours, with the distillation column at 150° C. The distillation column temperature was then increased to 200° C. and full vacuum (<0.5 mmHg) applied for 1 hour. The product was extruded through the die at the bottom of the reactor into a liquid nitrogen bath and isolated as a coarse white powder. Table 1 provides a comparison of the characterization data versus the processing conditions of the products obtained from the reactions described in Example 1 and Example 2.

The melt condensations as described above are thermodynamically controlled. Without taking any special precautions, such reactions typically will yield a statistical distribution of oligomeric chains with reactive hydroxyl groups at both ends, chains with one hydroxyl group at one end and a non-reactive phenyl group at the other end, or chains with two non-reactive phenyl groups at both end. Typically, using no special conditions, the amount of any of these three types of chains is less than 80%. Example 1 shows that the amount of bis-OH chains is only 72%, which is relatively low to be effectively used in e.g., epoxy applications. Using the specific reaction conditions as described in example 2, the amount of bis-OH chains is surprisingly high.

Example 3

Synthesis of Hydroxy-Terminated Co-Oligo(Phosphonate Carbonate)s

Linear hydroxy-terminated co-oligo(phosphonate carbonate)s were synthesized using a two-stage melt condensation process. Into a 12 L stainless steel reactor equipped with a mechanical stirrer and two reflux columns connected in series, 2,2-bis-(4-hydroxyphenyl) propane (BPA, 1800 g, 7.895 mol), diphenyl methylphosphonate (DPP) (457 g, 1.843 mol), diphenyl carbonate (DPC, 732 g, 3.421 mol) and the catalyst, tetraphenyl-phosphonium phenolate (TPPP (30% phenol), 0.51 g, 0.83 mmol) are added under nitrogen. The monomer/catalyst mixture was heated at 250° C. for 5 hours, with gradual reduction in the vacuum level to 10 mmHg. Both the top and bottom reflux columns were heated to 135° C. After 105 min, the temperature of the bottom column was increased to 150° C. and the top column decreased to 120° C. The phenol by-product was distilled off and collected in a graduated receiving flask. After 5 hours, the product was transferred via a stainless steel bridge to a 6 L stainless steel reactor held at 250° C. under nitrogen. At the start of the second stage, additional catalyst (0.51 g) was added to the reactor. The reaction was held at 250° C./10 mmHg for 2 hours, with the distillation column at 150° C. The distillation column temperature was increased to 200° C. and full vacuum (<0.5 mmHg) applied for 1 hour. The product was extruded through the die at the bottom of the reactor into a liquid nitrogen bath and isolated as a coarse white powder. Characterization: GPC(THF): Mw 2600, Mn 1300; Tg 85° C., 98% bis-OH (MALDI-TOF analysis). Surprisingly, the addition of DPC to the reaction mixture yields a composition with an extremely high level of oligophosphonates with at least two reactive hydroxyl groups.

Example 4

Synthesis of Hyper-Branched Hydroxy-Terminated Phosphonate Oligomers

Hyper-branched hydroxy-terminated oligophosphonates were synthesized via a two stage melt condensation process. The first stage was carried out in 12 L stainless steel reactor equipped with a mechanical stirrer and two reflux columns connected in series. To this reactor, 2,2-bis-(4-hydroxyphenyl) propane (BPA, 1764 g, 7.737 mol), diphenyl methylphosphonate (DPP) (1305 g, 5.262 mol), 1,1,1-tris(4-hydroxyphenyl)ethane (THPE) (48.1 g, 0.157 mol) and the catalyst, tetraphenylphosphonium phenolate (TPPP (30% phenol), 0.51 g, 0.83 mmol) were added under nitrogen. The monomer/catalyst mixture was heated at 265° C. for 5 hours, with gradual reduction in the vacuum level to 10 mmHg. Both the top and bottom reflux columns were heated to 135° C. After 105 minutes, the temperature of the bottom column was increased to 150° C. and the top column decreased to 120° C. The phenol by-product was distilled off and collected in a graduated receiving flask. After 5 hours, the product was transferred via a stainless steel bridge to a 6 L stainless steel reactor held at 265° C. under nitrogen. At the start of the second stage, additional catalyst (2.55 g) was added to the reactor. The reaction was held at 265° C./10 mmHg for 2 hours, with the distillation column at 150° C. The distillation column temperature was increased to 200° C. and full vacuum (<0.5 mmHg) applied for 1 hour. The product was extruded through the die at the bottom of the reactor into a liquid nitrogen bath and isolated as a coarse white powder. Characterization: GPC (THF): Mw 2700, Mn 1400; Tg 82° C.; hydroxyl number 76, 84% bis-OH, consisting of 4% branched OH terminated oligomers (MALDI analysis).

Example 5

Synthesis of Hyper-Branched Hydroxy-Terminated Phosphonate Oligomers

Hyper-branched hydroxy-terminated oligophosphonates were synthesized via a two stage melt condensation process. The first stage was carried out in 0.5 L glass reactor equipped with a mechanical stirrer and a reflux column. To this reactor, 2,2-bis-(4-hydroxyphenyl) propane (BPA, 95.4970 g, 0.4188 mol), diphenyl methylphosphonate (DPP) (84.6861 g, 0.3415 mol), 1,1,1-tris(4-hydroxyphenyl)ethane (THPE) (19.2780 g, 0.0630 mol) and the catalyst, tetraphenylphosphonium phenolate (TPPP (30% phenol), 0.4019 g, 0.63 mmol) were added under nitrogen. The monomer/catalyst mixture was heated at 265° C. for 5 hours, with gradual reduction in the vacuum level to 10 mmHg. The reflux column was heated to 135° C., and then decreased to 120° C. after 105 minutes. The phenol by-product was collected in a graduated receiving flask. After 5 hours, the reflux column was closed off and the reaction flask connected to a glass bridge column heated to 150° C. At the start of this second stage, additional catalyst (2.0096 g) was added to the reactor. The reaction was held at 265° C./10 mmHg for 1 hour, increased to 290° C. for 0.5 hours, and then to 300° C. at full vacuum for 10 minutes. The product was cooled to room temperature and isolated as a light brown solid. Characterization: GPC (THF): Mw 14,600, Mn 3700, PD 3.95, Tg 101° C.

Example 6

Synthesis of Hydroxy-Terminated Oligomers with Higher Mw

Phosphonate oligomers with hydroxyl end-groups and higher molecular weight (than in Example 2) were synthesized by changing the monomer stoichiometry and reactions conditions. In a 12 L stainless steel reactor equipped with a mechanical stirrer and two reflux columns connected in series, 2,2-bis-(4-hydroxyphenyl) propane (BPA, 1870 g, 8.202 mol), diphenyl methylphosphonate (DPP) (1695 g, 6.835 mol), and the catalyst, tetraphenylphosphonium phenolate (TPPP (30% phenol), 0.585 g, 0.95 mmol) were added under nitrogen. The monomer/catalyst mixture was heated at 265° C. for 5 hours, with gradual reduction in the vacuum level to 4 mmHg. Both the top and bottom reflux columns were heated to 135° C. After 105 min, the temperature of the bottom column was increased to 150° C. and the top column decreased to 120° C. The phenol by-product was distilled off and collected in a graduated receiving flask. After 5 hours, the product was transferred via a stainless steel bridge to a 6 L stainless steel reactor at 265° C. under nitrogen. The reaction temperature was increased to 300° C. and allowed to react for 1 hour under full vacuum (<0.5 mmHg). The distillation column was set to 200° C. The product is extruded through the die at the bottom of the reactor into a liquid nitrogen bath and isolated as a coarse white powder. Characterization: GPC (THF): Mw 4400, Mn 3000; Tg 78° C.; hydroxyl number 37 mg KOH/g.

Example 7

Synthesis of Epoxy-Terminated Phosphonate-Oligomers

Hydroxy-terminated phosphonate oligomers (Example 5) and an epoxy resin (digylcidyl ether of bisphenol A (Epon 828)) were reacted in a 1:2 ratio (based on reactive OH:epoxy equivalents). The oligomer was first melted at 140° C. before addition of the epoxy resin. After 30 minutes, the catalyst, 2-ethyl-4-methyl imidazole was added (0.1 phr) and allowed to react for another 1.5 hours. The product is a solid at room temperature and soluble in MEK and THF. GPC results of the product in THF: Mw 4900; Mn 3200.

Example 8

Preparation of Phosphonate-Based Prepolymers

A 50 wt. % solution of a hydroxy-terminated phosphonate oligomer (Example 5) was prepared in DPP by stirring at 100° C. for 6 hours. The solution was cooled to room temperature, yielding a slightly yellow, clear viscous fluid. The phosphonate oligomer solution in DPP was reacted with methylene diisocyanate in a 60:40 ratio (Oligomer:MDI) yielding a phosphonate-based prepolymer.

Example 9

Hydroxy-Terminated Oligomers in Polyurethane-Urea Coatings

Polyurethane-urea films were prepared by spraying a combination of the A-side (diisocyanates) and the B-side (diamines) onto primed concrete boards of 6 inches×18 inches for flammability testing (Scheme 1). The prepolymer 60/40 (Oligomer/MDI) prepared in Example 8 was added to the A-side at a 50% loading. The thickness of each coating was 90 mils (0.09 inches).

Scheme 1. Preparation of polyurethane-urea coatings

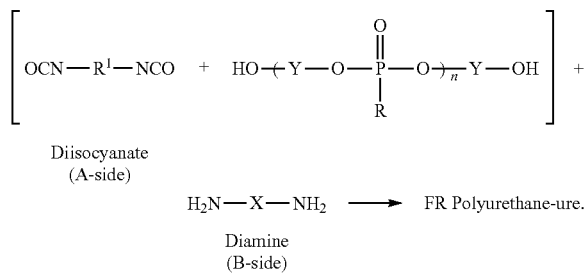

Diisocyanate
(A-side)

H₂N—X—NH₂ → FR Polyurethane-ure.

Diamine
(B-side)

Example 10

Testing of Flame Retardant (FR) Behavior of Polyurethane-Urea Coatings

FR testing was conducted in accordance with the ASTM E-162, "Standard Method of Test for Surface Flammability of Materials Using a Radiant Heat Energy Source." The spray-coated boards are mounted in a frame placed facing the radiant panel, but inclined at an angle of 30 degrees from top downward. A pilot burner adjusted to provide a 6" to 7" flame serves to ignite the sample at the top. The material under test burns downward and the results are recorded as a Flamespread Index (FSI) determined from progression time of the flame at 3, 6, 9, 12, and 15 inch interval marks measured from the top of the sample. The maximum temperature increase resulting from the burning sample was measured by 8 thermocouples connected in parallel and located in the sheet metal stack above the tested sample. The FSI is derived from the following formula:

$$Is = Fs \times Q$$

where Is is the Flamespread Index, Fs is the Flamespread Factor, and Q is the Heat Evolution Factor. The flamespread classification system used by most of the model building codes and the National Fire Protection Association Life Safety Code, NFPA No. 101, encompasses the following:

Class A (I)—0 to 25 Flamespread Index
Class B (II)—26 to 75 Flamespread Index
Class C (III)—76 to 100 Flamespread Index The results of FSI testing of polyurethane-urea coatings containing the phosphonate-polyol prepared in Example 9 are provided in Table 2.

TABLE 2

Flamespread Index (FSI) Results

| Sample | wt % oligomer in A-side | % P | FSI | Class |
|---|---|---|---|---|
| Control | 0 | 0 | 212 | Fail |
| FRX 1 | 7.5 | 1.4 | 73 | B |
| FRX 2 | 6.0 | 1.7 | 57 | B |

Example 11

Synthesis of Vinyl-Hydroxy Terminated Oligomers

Phosphonate oligomers with vinyl ester, isopropenyl end groups, and hydroxy end-groups were synthesized via a two-stage melt condensation process. The first stage was carried out in a 12 L stainless steel reactor equipped with a mechanical stirrer and two reflux columns connected in series. To this reactor, 2,2-bis-(4-hydroxyphenyl) propane (BPA, 1800 g, 7.895 mol), diphenyl methylphosphonate (DPP) (1305 g, 1.843 mol), and the catalyst, tetraphenylphosphonium phenolate (TPPP (30% phenol), 5.1 g, 8.3 mmol) were added under nitrogen. The monomer/catalyst mixture was heated at 265° C. for 5 hours, with gradual reduction in the vacuum level to 10 mmHg. Both the top and bottom reflux columns were heated to 135° C. After 105 min, the temperature of the bottom column was increased to 150° C., and the top column decreased to 120° C. The phenol by-product was distilled off and collected in a graduated receiving flask. After 5 hours, the product was transferred via a stainless steel bridge to a 6 L stainless steel reactor held at 265° C. under nitrogen. The reaction run at 265° C./10 mmHg for 2 hours, with the distillation column at 150° C. The distillation column temperature was then increased to 200° C. and full vacuum (<0.5 mmHg) applied for 1 hour. The product was extruded through the die at the bottom of the reactor into a liquid nitrogen bath and isolated as a coarse white powder. Characterization: GPC (THF): Mw 3100, Mn 1600; Tg 85° C.; % P 9.1, hydroxyl number 77 mg KOH/g, MALDI-6% vinyl ester end groups.

The invention claimed is:

1. A composition comprising hyperbranched oligophosphonates, each hyperbranched oligophosphonate having degree of branching from 0.05 to about 1.0 and wherein about 40% to about 98% the total of hyperbranched oligophosphonates have two or more reactive end-groups.

2. The composition of claim 1, wherein the reactive end-groups comprise hydroxyl end groups, epoxy end groups, vinyl end groups, vinyl ester end groups, isopropenyl end groups, isocyanate end groups, and combinations thereof.

3. The composition of claim 1, wherein the hyperbranched oligophosphonates comprise oligophosphonates, random co-oligo(phosphonate ester)s, block co-oligo(phosphonate ester)s, random co-oligo(phosphonate carbonate)s, block co-oligo(phosphonate carbonate)s, or combinations thereof.

4. The composition of claim 1, wherein the hyperbranched oligophosphonates comprises a number averaged molecular weight of from about 500 g/mole to about 5000 g/mole.

5. The composition of claim 1, wherein hyperbranched oligophosphonates comprise units derived from a bisphenol.

6. The composition of claim 1, wherein the hyperbranched oligophosphonates comprise from about 2 to about 20 units derived from a branching agent.

7. The composition of claim 1, wherein the hyperbranched oligophosphonates comprise units of Formula I:

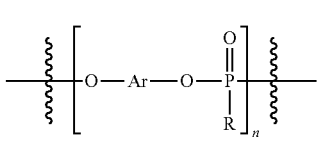

wherein:
Ar is an aromatic group and —O—Ar—O— is derived from is derived from a dihydroxy compound having one or more aryl rings;
R is a $C_{1-20}$ alkyl, $C_{2-20}$ alkene, $C_{2-20}$ alkyne, $C_{5-20}$ cycloalkyl, or $C_{6-20}$ aryl; and
n is an integer from 1 to about 10.

8. The composition of claim 7, wherein —O—Ar—O— is derived from hydroquinone, resorcinol, bisphenol A, bisphenol F, and 4,4'-biphenol, phenolphthalein, 4,4'-thiodiphenol, 4,4'-sulfonyldiphenol, 3,3,5-trimethylcyclohexyldiphenol, or combinations thereof.

9. The composition of claim 1, wherein the hyperbranched oligophosphonates comprise a structure of Formula VII:

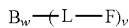

VII wherein:
B is the hyperbranched oligophosphonate;
w is the number of branches;
v is an integer that is not zero;
L is a linking group comprising an aryl group, heteroaryl group, or a covalent bond; and
F is a reactive group.

10. The composition of claim 9, wherein each F, independently, comprises hydroxyl, carboxylic acid, amine, cyanate, isocyanate, epoxy, glycidyl ether, vinyl, vinyl ester, isopropenyl, and the like and combinations thereof.

11. The composition of claim 9, wherein B comprises a structure of Formula IX or Formula X:

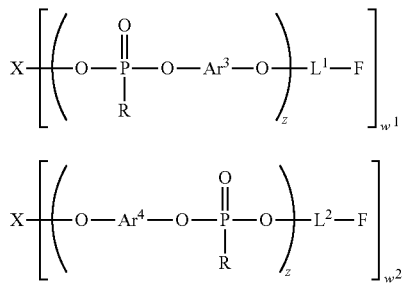

wherein:
each $Ar^3$ and $Ar^4$ is independently an aromatic group and each —O—$Ar^3$—O— and —O—$Ar^4$—O— is derived from a dihydroxy compound having one or more aryl rings;
each R is, independently, a $C_{1-20}$ alkyl, $C_{2-20}$ alkene, $C_{2-20}$ alkyne, $C_{5-20}$ cycloalkyl, or $C_{6-20}$ aryl;
each $L^2$ and $L^2$ is, independently, a covalent bond or single aryl groups, biaryl groups, triaryl groups, tetraaryl groups;
each F is, independently, a reactive group;
each X is, independently, a unit derived from a branching agent;
each z is, independently, an integer from 1 to about 10; and
each $w^1$ and $w^2$ is, independently, an integer from 1 to 5.

12. The composition of claim 11, wherein —O—$Ar^3$—O— and —O—$Ar^4$—O— is derived from resorcinol, hydroquinone, bisphenol A, bisphenol F, and 4,4'-biphenol, phenolphthalein, 4,4'-thiodiphenol, 4,4'-sulfonyldiphenol, 3,3,5-trimethylcyclohexyldiphenol, or combinations thereof.

13. The composition of claim 11, wherein R is methyl.

14. The composition of claim 11, wherein X is derived from a triaryl phosphate ester.

15. The composition of claim 14, wherein the triaryl phosphate ester comprises a compound of Formula VIII:

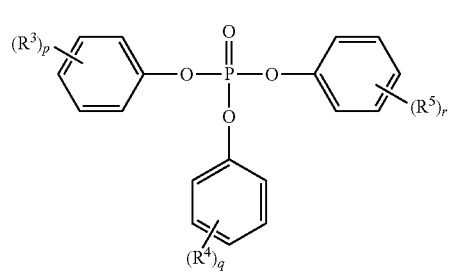

wherein
each $R^3$, $R^4$, and $R^5$ is, independently, hydrogen, $C_1$-$C_4$ alkyl; and
each of p, q, and r is, independently, an integer from 1 to 5.

16. The composition of claim 14, wherein X is derived from triphenyl phosphate.

17. The composition of claim 11, wherein two or more X are linked by a moiety of Formula XI, Formula XII, or Formula XIII or combinations thereof:

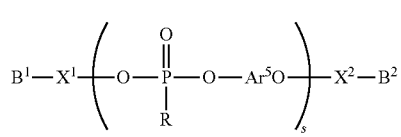

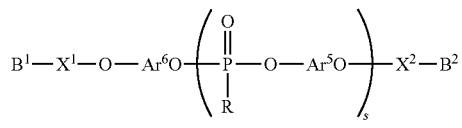

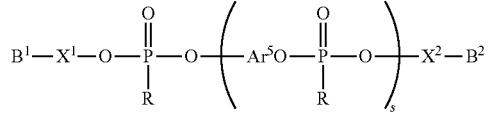

wherein:
each $B^1$ and $B^2$ is, independently, a hyperbranched oligophosphonate of Formula XI or Formula X;
each $Ar^5$ and $Ar^6$ is, independently, an aromatic group and each —O—$Ar^5$—O— and —O—$Ar^6$—O— is derived from a dihydroxy compound having one or more aryl rings;
each R is, independently, a $C_{1-20}$ alkyl, $C_{2-20}$ alkene, $C_{2-20}$ alkyne, $C_{5-20}$ cycloalkyl, or $C_6$-$C_{20}$ aryl;
each $X^1$ and $X^2$ is, independently, a unit derived from a branching agent; and
each s is, independently, an integer of from 1 to about 10.

18. A method for preparing a hyperbranched oligophosphonate comprising:
combining a phosphonate monomer, a branching agent, and co-monomer to create a monomer mixture, the monomer mixture comprising a molar excess of the co-monomer and from about 0.5 mole % to about 10 mole % or greater of the total monomer mixture of the branching agent;
heating the monomer mixture;

adding a polymerization catalyst to the monomer mixture to create a reaction mixture; and
maintaining a polymerization temperature.

19. The method of claim 18, wherein the phosphonate monomer comprises a monomer of Formula XIV:

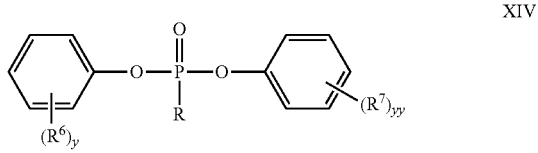

wherein:
each $R^6$ and each $R^7$ are, independently, hydrogen or $C_1$-$C_4$ alkyl;
y and yy are, independently, integers of 1 to 5; and
R is $C_1$-$C_4$ alkyl.

20. The method of claim 18, wherein the phosphonate monomer is selected from the group consisting of diphenyl methylphosphonic acid, methyldiphenoxyphosphine oxide, and combinations thereof.

21. The method of claim 18, wherein the co-monomer is selected from the group consisting of resorcinol, hydroquinone, bisphenol A, bisphenol F, and 4,4'-biphenol, phenolphthalein, 4,4'-thiodiphenol, 4,4'-sulfonyldiphenol, 3,3,5-trimethylcyclohexyldiphenol, and combinations thereof.

22. The method of claim 18, wherein the polymerization catalyst comprises tetraphenylphosphonium or a derivative thereof and an anion associated with the tetraphenylphosphonium selected from the group consisting of tetraaryl borohydride, a halide, and a substituted or unsubstituted phenolate group.

23. The method of claim 18, wherein the polymerization catalyst comprises tetraphenylphosphonium phenolate.

24. The method of claim 18, further comprising heating the monomer mixture and polymerization catalyst at a reduced pressure.

25. The method of claim 18, wherein heating comprises heating the reaction mixture to a temperature of from about 100° C. to about 350° C.

26. The method of claim 18, further comprising stopping heating when the evolution of phenol has stopped.

27. The method of claim 18, wherein the at least one branching agent is selected from the groups consisting of trimesic acid, pyromellitic acid, trimellitic anhydride, pyromellitic anhydride, trimethylolpropane, dimethyl hydroxyl terephthalate, pentaerythritol, phloroglucinol, 4,6-dimethyl-2,4,6-tri-(4-hydroxy phenyl)-2-heptene, 4,6-dimethyl-2,4,6-tri-(4-hydroxy phenyl)-heptane, 1,3,5-tri-(4-hydroxy phenyl)-benzene, 1,1,1-tri-(4-hydroxy phenyl)-ethane, tri-(4-hydroxy phenyl)-phenyl methane, 2,2-bis-[4,4-bis-(4-hydroxy phenyl)-cyclohexyl]-propane, 2,4-bis-(4-hydroxy phenyl)isopropyl phenol, 2,6-bis-(2'-hydroxy-5'-methyl benzyl)-4-methyl phenol 2-(4-hydroxy phenyl)-2-(2,4-dihydroxy phenol)-propane, tetra-(4-hydroxy phenyl)methane, tetra-[4-(4-hydroxy phenyl isopropyl)phenoxy]-methane, 1,4-bis-(4,4"-dihydroxy triphenyl methyl)-benzene, and combinations thereof.

28. The method of claim 18, wherein the monomer mixture further comprises oligocarbonates, carbonate monomers, oligoesters, ester monomers, or combinations thereof.

29. The method of claim 28, wherein the carbonate monomer is selected from the group consisting of diphenyl carbonate, 4-tert-butylphenyl-phenyl carbonate, di-(4-tert-butylphenyl)carbonate, biphenyl-4-yl-phenyl carbonate, di-(biphenyl-4-yl)carbonate, 4-(1-methyl-1-phenylethyl)-phenyl-phenyl carbonate, di-[4-(1-methyl-1-phenylethyl)-phenyl]carbonate, and combinations thereof.

30. A method for preparing a hyperbranched oligophosphonate comprising:
providing a predominately hydroxyl terminated hyperbranched oligophosphonate; and
combining the predominately hydroxyl terminated hyperbranched oligophosphonate with an effective amount of epichlorohydrin; and
maintaining reaction conditions to create a predominately epoxy terminated oligophosphonate.

31. The method of claim 30, wherein the predominately hydroxyl terminated hyperbranched oligophosphonate comprises an oligophosphonate, random co-oligo(phosphonate ester), block co-oligo(phosphonate ester), random co-oligo(phosphonate carbonate), or block co-oligo(phosphonate carbonate).

32. A polymer composition comprising:
hyperbranched oligophosphonates, each hyperbranched oligophosphonate having degree of branching from 0.05 to about 1.0 wherein about 40% to about 98% the total of hyperbranched oligophosphonates have two or more reactive end-groups; and
an engineering polymer.

33. The polymer composition of claim 32, wherein the engineering polymer comprises polycarbonates, epoxies, epoxy derived polymers, polyepoxies, benzoxazines, polyacrylates, polyacrylonitriles, polyesters, poly(ethylene terephthalate), poly(trimethylene terephthalate), poly(butylene terephthalate), unsaturated polyesters, polyamides, polystyrenes, high impact strength polystyrene, polyureas, polyurethanes, polyphosphonates, polyphosphates, poly(acrylonitrile butadiene styrene)s, polyimides, polyarylates, poly(arylene ether)s, polyethylenes, polypropylenes, polyphenylene sulfides, poly(vinyl ester)s, polyvinyl chlorides, bismaleimide polymers, polyanhydrides, liquid crystalline polymers, cellulose polymers, or combination thereof.

34. The polymer compositions of claim 32, further comprising fillers, chopped or continuous glass fiber, metal fibers, organic fibers, aramid fibers, carbon fibers, carbon nanofibers, or ceramic fibers, surfactants, organic binders, polymeric binders, crosslinking agents, coupling agents, diluents, anti-dripping agents, fluorinated polyolefins, silicones, lubricants, mould release agents, pentaerythritol tetrastearate, nucleating agents, anti-static agents, conductive blacks, carbon nanotubes, organic antistatics, polyalkylene ethers, alkylsulfonates, perfluor sulfonic acid, perfluorbutane sulfinic acid potassium salt, polyamide-containing polymers, catalysts, colorants, inks, dyes, antioxidants, stabilizers, metal phosphinates, melamine cyanurate, melamine derivatives, flame retardants, or combinations thereof.

35. An article of manufacture comprising hyperbranched oligophosphonates, each hyperbranched oligophosphonate having degree of branching from 0.05 to about 1.0 wherein about 40% to about 98% the total of hyperbranched oligophosphonates have two or more reactive end-groups.

36. The article of manufacture of claim 35, wherein the article of manufacture is selected from the group consisting of coatings on plastics, coatings on metals, coatings on ceramic, coatings on wood products, free-standing films, fibers, foams, molded articles, fiber reinforced composites, support parts, electrical components, electrical connectors, laminated boards, laminated circuit boards, printed wiring laminated boards, housings, subcomponents and components for electrical devices, televisions, computers, laptop computers, printers, cell phones, video games, DVD players, and stereos.

37. The article of manufacture of claim 35, wherein the article of manufacture is laminate or a fiber reinforced composite used in electrical components, electrical connectors, printed wiring boards, printed circuit boards, televisions, computers, laptop computers, printers, copiers, scanners, cell phones, video games, DVD players, stereos, digital music players, hand held video players, or touch screens.

* * * * *

UNITED STATES PATENT AND TRADEMARK OFFICE
CERTIFICATE OF CORRECTION

PATENT NO. : 8,530,044 B2  
APPLICATION NO. : 13/335146  
DATED : September 10, 2013  
INVENTOR(S) : Kagumba et al.

Page 1 of 1

It is certified that error appears in the above-identified patent and that said Letters Patent is hereby corrected as shown below:

In the Claims:

In Column 36, lines 60 and 61, delete "is derived from" (second occurrence).

In Column 37, line 49, delete "$L^2$ and $L^2$" and insert -- $L^1$ and $L^2$ -- therefor.

Signed and Sealed this  
Twenty-fourth Day of June, 2014

Michelle K. Lee  
*Deputy Director of the United States Patent and Trademark Office*